(12) United States Patent
Reglos et al.

(10) Patent No.: US 7,935,134 B2
(45) Date of Patent: May 3, 2011

(54) SYSTEMS AND METHODS FOR STABILIZATION OF BONE STRUCTURES

(75) Inventors: Joey Camia Reglos, Lake Forest, CA (US); Moti Altarac, Irvine, CA (US); Stanley Kyle Hayes, Mission Viejo, CA (US); Shawn Tebbe, Oceanside, CA (US); Daniel H. Kim, Los Altos, CA (US); J. Christopher Flaherty, Topsfield, MA (US)

(73) Assignee: Exactech, Inc., Gainesville, FL (US)

( * ) Notice: Subject to any disclaimer, the term of this patent is extended or adjusted under 35 U.S.C. 154(b) by 659 days.

(21) Appl. No.: 11/427,738

(22) Filed: Jun. 29, 2006

(65) Prior Publication Data
US 2007/0100341 A1     May 3, 2007

Related U.S. Application Data

(63) Continuation-in-part of application No. 11/436,407, filed on May 17, 2006, which is a continuation-in-part of application No. 11/033,452, filed on Jan. 10, 2005, which is a continuation-in-part of application No. 11/006,495, filed on Dec. 6, 2004, and a continuation-in-part of application No. 10/970,366, filed on Oct. 20, 2004.

(51) Int. Cl.
*A61B 17/70* (2006.01)
(52) U.S. Cl. ......... 606/257; 606/254; 606/259; 606/260
(58) Field of Classification Search ........... 606/254–260
See application file for complete search history.

(56) References Cited

U.S. PATENT DOCUMENTS

| | | | |
|---|---|---|---|
| 602,580 A | 4/1898 | Haskins et al. | |
| 802,844 A | 10/1905 | Covell et al. | |
| 3,807,394 A * | 4/1974 | Attenborough | 606/60 |
| 4,611,582 A | 9/1986 | Duff | |
| 4,743,260 A | 5/1988 | Burton | |
| 5,015,247 A | 5/1991 | Michelson | |
| 5,092,866 A | 3/1992 | Breard et al. | |
| 5,129,388 A | 7/1992 | Vignaud et al. | |
| 5,171,279 A | 12/1992 | Mathews | |
| 5,180,393 A | 1/1993 | Commarmond | |
| 5,282,863 A | 2/1994 | Burton | |
| 5,368,594 A | 11/1994 | Martin et al. | |

(Continued)

FOREIGN PATENT DOCUMENTS
EP     767636     1/1999

(Continued)

OTHER PUBLICATIONS
U.S. Appl. No. 60/701,660.

(Continued)

*Primary Examiner* — Eduardo C Robert
*Assistant Examiner* — Andrew Yang
(74) *Attorney, Agent, or Firm* — Meyertons, Hood, Kivlin, Kowert & Goetzel, P.C.; Eric B. Meyertons

(57) ABSTRACT

A dynamic bone stabilization system is provided. The system may be placed through small incisions and tubes. The system provides systems and methods of treating the spine, which eliminate pain and enable spinal motion, which effectively mimics that of a normally functioning spine. Methods are also provided for stabilizing the spine and for implanting the subject systems.

23 Claims, 19 Drawing Sheets

U.S. PATENT DOCUMENTS

| | | | |
|---|---|---|---|
| 5,375,823 A | 12/1994 | Navas | |
| 5,387,212 A | 2/1995 | Yuan et al. | |
| 5,415,661 A | 5/1995 | Holmes | |
| 5,437,669 A | 8/1995 | Yuan et al. | |
| 5,437,672 A | 8/1995 | Alleyne | |
| 5,443,467 A | 8/1995 | Biedermann et al. | |
| 5,474,555 A | 12/1995 | Puno et al. | |
| 5,480,401 A | 1/1996 | Navas | |
| 5,484,437 A | 1/1996 | Michelson | |
| 5,489,308 A | 2/1996 | Kuslich et al. | |
| 5,522,843 A | 6/1996 | Zang | |
| 5,527,312 A | 6/1996 | Ray | |
| 5,540,688 A | 7/1996 | Navas | |
| 5,571,191 A | 11/1996 | Fitz | |
| 5,609,636 A | 3/1997 | Kohrs et al. | |
| 5,616,142 A | 4/1997 | Yuan et al. | |
| 5,645,599 A | 7/1997 | Samani | |
| 5,658,337 A | 8/1997 | Kohrs et al. | |
| 5,672,175 A | 9/1997 | Martin | |
| 5,720,751 A | 2/1998 | Jackson | |
| 5,741,253 A | 4/1998 | Michelson | |
| 5,776,135 A | 7/1998 | Errico et al. | |
| RE36,211 E | 5/1999 | Nonomura | |
| 5,964,761 A | 10/1999 | Kambin | |
| 6,014,588 A | 1/2000 | Fitz | |
| 6,033,406 A | 3/2000 | Mathews | |
| RE36,758 E | 6/2000 | Fitz | |
| 6,080,155 A | 6/2000 | Michelson | |
| 6,080,157 A | 6/2000 | Cathro et al. | |
| 6,083,224 A | 7/2000 | Gertzbein et al. | |
| 6,096,038 A | 8/2000 | Michelson | |
| 6,132,464 A | 10/2000 | Martin | |
| 6,200,322 B1 | 3/2001 | Branch et al. | |
| 6,241,730 B1 | 6/2001 | Alby | |
| 6,264,656 B1 | 7/2001 | Michelson | |
| 6,267,764 B1 * | 7/2001 | Elberg | 606/255 |
| 6,267,765 B1 | 7/2001 | Taylor et al. | |
| 6,270,498 B1 | 8/2001 | Michelson | |
| 6,273,914 B1 | 8/2001 | Papas | |
| 6,287,764 B1 | 9/2001 | Hildebrand et al. | |
| 6,419,703 B1 | 7/2002 | Fallin et al. | |
| 6,485,518 B1 | 11/2002 | Cornwall et al. | |
| 6,530,929 B1 | 3/2003 | Justis et al. | |
| 6,540,747 B1 | 4/2003 | Marino | |
| 6,547,795 B2 | 4/2003 | Schneiderman | |
| 6,558,390 B2 | 5/2003 | Cragg | |
| 6,562,038 B1 | 5/2003 | Morrison | |
| 6,562,046 B2 | 5/2003 | Sasso | |
| 6,565,605 B2 | 5/2003 | Goble et al. | |
| 6,579,319 B2 | 6/2003 | Goble et al. | |
| 6,610,091 B1 | 8/2003 | Reiley | |
| 6,626,904 B1 | 9/2003 | Jammet et al. | |
| 6,626,905 B1 | 9/2003 | Schmiel et al. | |
| 6,626,944 B1 | 9/2003 | Taylor | |
| 6,645,248 B2 | 11/2003 | Casutt | |
| 6,669,697 B1 | 12/2003 | Pisharodi | |
| 6,669,729 B2 | 12/2003 | Chin | |
| 6,695,842 B2 | 2/2004 | Zucherman et al. | |
| 6,716,245 B2 | 4/2004 | Pasquet et al. | |
| 6,749,613 B1 | 6/2004 | Conchy et al. | |
| 6,749,614 B2 | 6/2004 | Teitelbaum et al. | |
| 6,761,720 B1 | 7/2004 | Senegas | |
| 6,783,527 B2 | 8/2004 | Drewry et al. | |
| 6,802,844 B2 | 10/2004 | Ferree | |
| 6,802,845 B2 | 10/2004 | Shirado et al. | |
| 6,805,697 B1 | 10/2004 | Helm et al. | |
| 6,811,567 B2 | 11/2004 | Reiley | |
| 6,821,277 B2 | 11/2004 | Teitelbaum | |
| 6,835,205 B2 | 12/2004 | Atkinson et al. | |
| 6,835,207 B2 | 12/2004 | Zacouto et al. | |
| 6,875,212 B2 | 4/2005 | Shaolian et al. | |
| 6,899,716 B2 | 5/2005 | Cragg | |
| 6,902,580 B2 | 6/2005 | Fallin et al. | |
| 6,949,123 B2 | 9/2005 | Reiley | |
| 6,966,910 B2 | 11/2005 | Ritland | |
| 6,966,930 B2 | 11/2005 | Arnin et al. | |
| 6,974,478 B2 | 12/2005 | Reiley et al. | |
| 6,986,771 B2 | 1/2006 | Paul et al. | |
| 6,989,011 B2 | 1/2006 | Paul et al. | |
| 6,991,632 B2 | 1/2006 | Ritland | |
| 7,011,660 B2 | 3/2006 | Sherman et al. | |
| 7,011,685 B2 | 3/2006 | Arnin et al. | |
| 7,029,475 B2 | 4/2006 | Panjabi | |
| 7,051,451 B2 | 5/2006 | Augostino et al. | |
| 7,052,497 B2 | 5/2006 | Sherman et al. | |
| 7,056,321 B2 | 6/2006 | Pagliuca et al. | |
| 7,060,068 B2 | 6/2006 | Tromanhauser et al. | |
| 7,066,957 B2 | 6/2006 | Graf | |
| 7,070,598 B2 | 7/2006 | Lim et al. | |
| 7,074,238 B2 | 7/2006 | Stinson et al. | |
| 7,079,883 B2 | 7/2006 | Marino et al. | |
| 7,083,621 B2 | 8/2006 | Shaolian et al. | |
| 7,083,622 B2 | 8/2006 | Simonson | |
| 7,083,649 B2 | 8/2006 | Zucherman et al. | |
| 7,087,055 B2 | 8/2006 | Lim et al. | |
| 7,090,698 B2 | 8/2006 | Goble et al. | |
| 7,108,705 B2 | 9/2006 | Davison et al. | |
| 7,125,410 B2 | 10/2006 | Freudiger | |
| 7,137,985 B2 | 11/2006 | Jahng | |
| 7,182,783 B2 | 2/2007 | Trieu | |
| 7,188,626 B2 | 3/2007 | Foley et al. | |
| 7,207,992 B2 | 4/2007 | Ritland | |
| 7,229,441 B2 | 6/2007 | Trieu et al. | |
| 7,252,673 B2 | 8/2007 | Lim | |
| 7,282,065 B2 | 10/2007 | Kirschman | |
| 7,294,129 B2 | 11/2007 | Hawkins et al. | |
| 7,306,603 B2 | 12/2007 | Boehm, Jr. et al. | |
| 7,329,258 B2 | 2/2008 | Studer et al. | |
| 7,335,200 B2 | 2/2008 | Carli et al. | |
| 7,341,587 B2 | 3/2008 | Molz, IV et al. | |
| 7,354,453 B2 | 4/2008 | McAfee | |
| 7,377,921 B2 | 5/2008 | Studer et al. | |
| 7,377,942 B2 | 5/2008 | Berry | |
| 7,406,775 B2 | 8/2008 | Funk et al. | |
| 7,691,131 B2 | 4/2010 | Graf | |
| 2001/0037111 A1 | 11/2001 | Dixon et al. | |
| 2002/0065557 A1 | 5/2002 | Goble et al. | |
| 2002/0068975 A1 | 6/2002 | Teitelbaum et al. | |
| 2002/0072800 A1 | 6/2002 | Goble et al. | |
| 2002/0082600 A1 | 6/2002 | Shaolian et al. | |
| 2002/0095154 A1 | 7/2002 | Atkinson | |
| 2002/0120270 A1 | 8/2002 | Trieu et al. | |
| 2002/0123806 A1 | 9/2002 | Reiley | |
| 2002/0133155 A1 | 9/2002 | Ferree | |
| 2002/0151895 A1 | 10/2002 | Soboleski et al. | |
| 2002/0198526 A1 | 12/2002 | Shaolian et al. | |
| 2003/0004572 A1 | 1/2003 | Goble et al. | |
| 2003/0028250 A1 | 2/2003 | Reiley et al. | |
| 2003/0032965 A1 | 2/2003 | Schneiderman | |
| 2003/0040797 A1 | 2/2003 | Fallin et al. | |
| 2003/0055427 A1 | 3/2003 | Graf | |
| 2003/0093078 A1 | 5/2003 | Ritland | |
| 2003/0171749 A1 | 9/2003 | Le Couedic et al. | |
| 2003/0171750 A1 | 9/2003 | Chin | |
| 2003/0208202 A1 | 11/2003 | Falahee | |
| 2003/0208203 A1 | 11/2003 | Lim et al. | |
| 2003/0220642 A1 | 11/2003 | Freudiger | |
| 2003/0220643 A1 * | 11/2003 | Ferree | 606/61 |
| 2003/0229347 A1 | 12/2003 | Sherman et al. | |
| 2003/0236520 A1 | 12/2003 | Lim et al. | |
| 2004/0002708 A1 | 1/2004 | Ritland | |
| 2004/0006341 A1 | 1/2004 | Shaolian et al. | |
| 2004/0006344 A1 | 1/2004 | Nguyen et al. | |
| 2004/0039384 A1 | 2/2004 | Boehm et al. | |
| 2004/0049189 A1 | 3/2004 | Le Couedic et al. | |
| 2004/0064140 A1 | 4/2004 | Taylor et al. | |
| 2004/0073215 A1 | 4/2004 | Carli | |
| 2004/0080418 A1 | 4/2004 | Dahlborn et al. | |
| 2004/0082954 A1 | 4/2004 | Teitelbaum et al. | |
| 2004/0087947 A1 | 5/2004 | Lim et al. | |
| 2004/0092931 A1 | 5/2004 | Taylor et al. | |
| 2004/0116927 A1 | 6/2004 | Graf | |
| 2004/0127989 A1 | 7/2004 | Dooris et al. | |
| 2004/0138662 A1 | 7/2004 | Landry et al. | |
| 2004/0143265 A1 | 7/2004 | Landry et al. | |
| 2004/0143270 A1 | 7/2004 | Zucherman et al. | |
| 2004/0147928 A1 | 7/2004 | Landry et al. | |

| | | | | | | |
|---|---|---|---|---|---|---|
| 2004/0193158 A1 | 9/2004 | Lim et al. | | 2005/0203513 A1 | 9/2005 | Jahng et al. |
| 2004/0215190 A1 | 10/2004 | Nguyen et al. | | 2005/0203514 A1 | 9/2005 | Jahng et al. |
| 2004/0225289 A1 | 11/2004 | Biedermann et al. | | 2005/0203517 A1 | 9/2005 | Jahng et al. |
| 2004/0230201 A1 | 11/2004 | Yuan et al. | | 2005/0209593 A1 | 9/2005 | Kolb |
| 2004/0230304 A1 | 11/2004 | Yuan et al. | | 2005/0209694 A1 | 9/2005 | Loeb |
| 2004/0236328 A1 | 11/2004 | Paul et al. | | 2005/0215999 A1 | 9/2005 | Birkmeyer et al. |
| 2004/0236329 A1 | 11/2004 | Panjabi | | 2005/0216000 A1 | 9/2005 | Colleran et al. |
| 2004/0267260 A1 | 12/2004 | Mack et al. | | 2005/0222569 A1 | 10/2005 | Panjabi |
| 2005/0010217 A1 | 1/2005 | Dalton | | 2005/0234551 A1 | 10/2005 | Fallin et al. |
| 2005/0010953 A1 | 1/2005 | Carney et al. | | 2005/0235508 A1 | 10/2005 | Augostino et al. |
| 2005/0010954 A1 | 1/2005 | Binder | | 2005/0240264 A1 | 10/2005 | Tokish, Jr. et al. |
| 2005/0010956 A1 | 1/2005 | Moon et al. | | 2005/0240265 A1 | 10/2005 | Kuiper et al. |
| 2005/0021031 A1 | 1/2005 | Foley et al. | | 2005/0245928 A1 | 11/2005 | Colleran et al. |
| 2005/0027361 A1 | 2/2005 | Reiley | | 2005/0245930 A1 | 11/2005 | Timm et al. |
| 2005/0033295 A1 | 2/2005 | Wisnewski | | 2005/0261682 A1 | 11/2005 | Ferree |
| 2005/0033434 A1 | 2/2005 | Berry | | 2005/0273167 A1 | 12/2005 | Triplett et al. |
| 2005/0033439 A1 | 2/2005 | Gordon et al. | | 2005/0277921 A1 | 12/2005 | Eisermann et al. |
| 2005/0038432 A1 | 2/2005 | Shaolian et al. | | 2005/0277922 A1 | 12/2005 | Trieu et al. |
| 2005/0038440 A1 | 2/2005 | Larson et al. | | 2005/0288670 A1 | 12/2005 | Panjabi et al. |
| 2005/0043742 A1 | 2/2005 | Bruneau et al. | | 2006/0015100 A1 | 1/2006 | Panjabi et al. |
| 2005/0043797 A1 | 2/2005 | Lee | | 2006/0036240 A1 | 2/2006 | Colleran et al. |
| 2005/0043799 A1 | 2/2005 | Reiley | | 2006/0036244 A1 | 2/2006 | Spitler et al. |
| 2005/0049705 A1 | 3/2005 | Hale et al. | | 2006/0036255 A1 | 2/2006 | Pond et al. |
| 2005/0049708 A1 | 3/2005 | Atkinson et al. | | 2006/0052785 A1 | 3/2006 | Augostino et al. |
| 2005/0055096 A1 | 3/2005 | Serhan et al. | | 2006/0058791 A1 | 3/2006 | Broman et al. |
| 2005/0056979 A1 | 3/2005 | Studer et al. | | 2006/0079894 A1 | 4/2006 | Colleran et al. |
| 2005/0065514 A1 | 3/2005 | Studer | | 2006/0084976 A1 | 4/2006 | Borgstrom et al. |
| 2005/0065515 A1 | 3/2005 | Jahng | | 2006/0084982 A1 | 4/2006 | Kim |
| 2005/0065516 A1 | 3/2005 | Jahng | | 2006/0084984 A1 | 4/2006 | Kim |
| 2005/0065517 A1 | 3/2005 | Chin | | 2006/0084987 A1 | 4/2006 | Kim |
| 2005/0070917 A1 | 3/2005 | Justis | | 2006/0084991 A1 | 4/2006 | Borgstrom et al. |
| 2005/0080418 A1 | 4/2005 | Simonson et al. | | 2006/0085072 A1 | 4/2006 | Funk et al. |
| 2005/0080486 A1 | 4/2005 | Fallin et al. | | 2006/0106380 A1* | 5/2006 | Colleran et al. ............... 606/61 |
| 2005/0085813 A1 | 4/2005 | Spitler et al. | | 2006/0106394 A1 | 5/2006 | Colleran |
| 2005/0085815 A1 | 4/2005 | Harms et al. | | 2006/0142759 A1 | 6/2006 | Arnin et al. |
| 2005/0085912 A1 | 4/2005 | Arnin et al. | | 2006/0149238 A1 | 7/2006 | Sherman et al. |
| 2005/0101953 A1 | 5/2005 | Simonson | | 2006/0149239 A1 | 7/2006 | Winslow et al. |
| 2005/0101956 A1 | 5/2005 | Simonson | | 2006/0149254 A1 | 7/2006 | Lauryssen et al. |
| 2005/0102028 A1 | 5/2005 | Arnin et al. | | 2006/0149272 A1 | 7/2006 | Winslow et al. |
| 2005/0113927 A1 | 5/2005 | Malek | | 2006/0149289 A1 | 7/2006 | Winslow et al. |
| 2005/0119748 A1 | 6/2005 | Reiley et al. | | 2006/0149373 A1 | 7/2006 | Winslow et al. |
| 2005/0124991 A1 | 6/2005 | Jahng | | 2006/0149374 A1 | 7/2006 | Winslow et al. |
| 2005/0125066 A1 | 6/2005 | McAfee | | 2006/0149375 A1 | 7/2006 | Yuan et al. |
| 2005/0131405 A1 | 6/2005 | Molz, IV et al. | | 2006/0149383 A1 | 7/2006 | Arnin et al. |
| 2005/0131406 A1 | 6/2005 | Reiley et al. | | 2006/0173454 A1 | 8/2006 | Spitler et al. |
| 2005/0131407 A1 | 6/2005 | Sicvol et al. | | 2006/0189983 A1 | 8/2006 | Fallin et al. |
| 2005/0131408 A1 | 6/2005 | Sicvol et al. | | 2006/0189984 A1 | 8/2006 | Fallin et al. |
| 2005/0131409 A1 | 6/2005 | Chervitz et al. | | 2006/0190083 A1 | 8/2006 | Arnin et al. |
| 2005/0131422 A1 | 6/2005 | Anderson et al. | | 2006/0195086 A1 | 8/2006 | Sybert |
| 2005/0131537 A1 | 6/2005 | Hoy et al. | | 2006/0195088 A1 | 8/2006 | Sacher et al. |
| 2005/0131538 A1 | 6/2005 | Chervitz et al. | | 2006/0200137 A1 | 9/2006 | Soboleski et al. |
| 2005/0131545 A1 | 6/2005 | Chervitz et al. | | 2006/0217718 A1 | 9/2006 | Chervitz et al. |
| 2005/0143737 A1 | 6/2005 | Pafford et al. | | 2006/0217719 A1 | 9/2006 | Albert et al. |
| 2005/0143823 A1 | 6/2005 | Boyd et al. | | 2006/0235388 A1 | 10/2006 | Justis et al. |
| 2005/0149020 A1 | 7/2005 | Jahng | | 2006/0235414 A1 | 10/2006 | Lim et al. |
| 2005/0154390 A1* | 7/2005 | Biedermann et al. ............ 606/61 | | 2006/0241642 A1 | 10/2006 | Arnin et al. |
| 2005/0154461 A1 | 7/2005 | Humphreys et al. | | 2006/0241758 A1 | 10/2006 | Peterman et al. |
| 2005/0154464 A1 | 7/2005 | Humphreys et al. | | 2006/0241759 A1 | 10/2006 | Trieu |
| 2005/0154465 A1 | 7/2005 | Hodges et al. | | 2006/0241768 A1 | 10/2006 | Trieu |
| 2005/0154466 A1 | 7/2005 | Humphreys et al. | | 2006/0241769 A1 | 10/2006 | Gordon et al. |
| 2005/0154467 A1 | 7/2005 | Peterman et al. | | 2006/0247623 A1 | 11/2006 | Anderson et al. |
| 2005/0165396 A1* | 7/2005 | Fortin et al. ..................... 606/61 | | 2006/0247632 A1 | 11/2006 | Winslow et al. |
| 2005/0171543 A1 | 8/2005 | Timm et al. | | 2006/0247633 A1 | 11/2006 | Winslow et al. |
| 2005/0171608 A1 | 8/2005 | Peterman et al. | | 2006/0247637 A1 | 11/2006 | Colleran et al. |
| 2005/0171609 A1 | 8/2005 | Humphreys et al. | | 2006/0247650 A1 | 11/2006 | Yerby et al. |
| 2005/0171610 A1 | 8/2005 | Humphreys et al. | | 2006/0247769 A1 | 11/2006 | Molz et al. |
| 2005/0177156 A1 | 8/2005 | Timm et al. | | 2006/0247773 A1 | 11/2006 | Stamp |
| 2005/0177157 A1 | 8/2005 | Jahng | | 2006/0260483 A1 | 11/2006 | Hartmann et al. |
| 2005/0177164 A1 | 8/2005 | Walters et al. | | 2006/0264934 A1 | 11/2006 | Fallin |
| 2005/0177166 A1 | 8/2005 | Timm et al. | | 2006/0264962 A1 | 11/2006 | Chin et al. |
| 2005/0177240 A1 | 8/2005 | Blain | | 2006/0265074 A1 | 11/2006 | Krishna et al. |
| 2005/0182400 A1 | 8/2005 | White | | 2006/0271198 A1 | 11/2006 | McAfee |
| 2005/0182401 A1 | 8/2005 | Timm et al. | | 2006/0276801 A1 | 12/2006 | Yerby et al. |
| 2005/0182409 A1 | 8/2005 | Callahan et al. | | 2006/0276897 A1 | 12/2006 | Winslow et al. |
| 2005/0187548 A1 | 8/2005 | Butler | | 2006/0282075 A1 | 12/2006 | Labrom et al. |
| 2005/0192574 A1 | 9/2005 | Blain | | 2006/0282077 A1 | 12/2006 | Labrom et al. |
| 2005/0197700 A1 | 9/2005 | Boehm, Jr. et al. | | 2006/0282078 A1 | 12/2006 | Labrom et al. |
| 2005/0197705 A1 | 9/2005 | Arnin et al. | | 2006/0282079 A1 | 12/2006 | Labrom et al. |
| 2005/0203511 A1 | 9/2005 | Wilson-MacDonald et al. | | 2006/0282080 A1 | 12/2006 | Albert et al. |

| | | | |
|---|---|---|---|
| 2006/0293657 A1 | 12/2006 | Hartmann | |
| 2007/0005062 A1 | 1/2007 | Lange et al. | |
| 2007/0005063 A1 | 1/2007 | Bruneau et al. | |
| 2007/0016191 A1 | 1/2007 | Culbert et al. | |
| 2007/0016193 A1 | 1/2007 | Ritland | |
| 2007/0016195 A1 | 1/2007 | Winslow et al. | |
| 2007/0016196 A1 | 1/2007 | Winslow et al. | |
| 2007/0016218 A1 | 1/2007 | Winslow et al. | |
| 2007/0016296 A1 | 1/2007 | Triplett et al. | |
| 2007/0043358 A1 | 2/2007 | Molz et al. | |
| 2007/0043359 A1 | 2/2007 | Altarac | |
| 2007/0049931 A1 | 3/2007 | Justis et al. | |
| 2007/0055257 A1 | 3/2007 | Vaccaro et al. | |
| 2007/0073289 A1 | 3/2007 | Kwak et al. | |
| 2007/0100341 A1 | 5/2007 | Reglos et al. | |
| 2007/0118122 A1 | 5/2007 | Butler et al. | |
| 2007/0161988 A1 | 7/2007 | Drewry et al. | |
| 2007/0161997 A1 | 7/2007 | Thramann et al. | |
| 2007/0239159 A1 | 10/2007 | Altarac et al. | |
| 2008/0045951 A1 | 2/2008 | Fanger et al. | |
| 2008/0097441 A1 | 4/2008 | Hayes et al. | |
| 2008/0262554 A1 | 10/2008 | Hayes et al. | |
| 2009/0030465 A1 | 1/2009 | Altarac et al. | |
| 2009/0228045 A1 | 9/2009 | Hayes et al. | |
| 2010/0036423 A1 | 2/2010 | Hayes et al. | |

FOREIGN PATENT DOCUMENTS

| | | |
|---|---|---|
| EP | 0951246 | 10/1999 |
| EP | 0986339 | 3/2000 |
| EP | 1056408 | 12/2000 |
| EP | 1138268 | 10/2001 |
| EP | 1145602 | 10/2001 |
| EP | 1303225 | 4/2003 |
| EP | 1399078 | 3/2004 |
| EP | 1415602 | 5/2004 |
| EP | 1415603 | 7/2005 |
| EP | 1810624 | 7/2007 |
| FR | 2728454 | 6/1996 |
| WO | WO-9116018 | 10/1991 |
| WO | WO-9426192 | 11/1994 |
| WO | WO-9600049 | 1/1996 |
| WO | WO-9848717 | 11/1998 |
| WO | WO-9855038 | 12/1998 |
| WO | WO-0130248 | 5/2001 |
| WO | WO-0141681 | 6/2001 |
| WO | WO-0062684 | 2/2002 |
| WO | WO-0238060 | 5/2002 |
| WO | WO-02065954 | 8/2002 |
| WO | WO-02067793 | 9/2002 |
| WO | WO-02102259 | 12/2002 |
| WO | WO-03047442 | 6/2003 |
| WO | WO-03075805 | 9/2003 |
| WO | WO-03094699 | 11/2003 |
| WO | WO-03101350 | 12/2003 |
| WO | WO-2004008949 | 1/2004 |
| WO | WO-2004047617 | 6/2004 |
| WO | WO-2005030029 | 4/2005 |
| WO | WO-2005030031 | 4/2005 |
| WO | WO-2005030066 | 4/2005 |
| WO | WO-2005030067 | 4/2005 |
| WO | WO-2005041799 | 5/2005 |
| WO | WO-2005044152 | 5/2005 |
| WO | WO-2005046515 | 5/2005 |
| WO | WO-2005053572 | 6/2005 |
| WO | WO-2005055874 | 6/2005 |
| WO | 2005/065516 | 7/2005 |
| WO | WO-2005067824 | 7/2005 |
| WO | WO-2005070278 | 8/2005 |
| WO | WO-2005070349 | 8/2005 |
| WO | WO-2005070350 | 8/2005 |
| WO | WO-2005070351 | 8/2005 |
| WO | WO-2005070352 | 8/2005 |
| WO | WO-2005070353 | 8/2005 |
| WO | WO-2005070354 | 8/2005 |
| WO | WO-2005077113 | 8/2005 |
| WO | WO-2005079426 | 9/2005 |
| WO | WO-2005079672 | 9/2005 |
| WO | WO-2005079711 | 9/2005 |
| WO | WO-2005084590 | 9/2005 |
| WO | WO-2005087121 | 9/2005 |
| WO | WO-2005092223 | 10/2005 |
| WO | WO-2005094704 | 10/2005 |
| WO | WO-2006016371 | 2/2006 |
| WO | WO-2006017507 | 2/2006 |
| WO | 2006/045091 | 4/2006 |
| WO | WO-2006042188 | 4/2006 |
| WO | WO-2006042189 | 4/2006 |
| WO | WO-2006047363 | 5/2006 |
| WO | WO-2006063107 | 6/2006 |
| WO | WO-2006102443 | 9/2006 |
| WO | WO-2006108067 | 10/2006 |
| WO | WO-2006125142 A2 | 11/2006 |
| WO | 2007/014119 | 2/2007 |
| WO | WO-2007021588 | 2/2007 |
| WO | WO-2007075375 | 7/2007 |
| WO | 2007/117366 | 10/2007 |
| WO | 2007/136612 | 11/2007 |
| WO | 2008/069835 | 6/2008 |
| WO | 2008/153747 | 12/2008 |
| WO | 2009/042489 | 4/2009 |
| WO | 2009/100190 | 8/2009 |
| WO | 2010/019791 | 2/2010 |

OTHER PUBLICATIONS

Non-Final Office Action for U.S. Appl. No. 11/006,495, Mail Date Jun. 30, 2008, 27 pages.
International Search Report and Written Opinion for application No. PCT/US06/28586, Mail Date Jul. 27, 2007, 14 pages.
International Search Report and Written Opinion for application No. PCT/US07/04726, Mail Date Jul. 8, 2008, 7 pages.
International Search Report and Written Opinion for application No. PCT/US05/38021, Mail Date Apr. 10, 2006, 7 pages.
International Search Report and Written Opinion for application No. PCT/US07/11573, Mail Date Apr. 23, 2008, 8 pages.
Final Office Action for U.S. Appl. No. 10/970,366, Mail Date: Oct. 5, 2009, 8 pages.
Non-Final Office Action for U.S. Appl. No. 10/970,366, Mail Date: Nov. 25, 2008, 7 pages.
Non-Final Office Action for U.S. Appl. No. 11/006,495, Mail Date: Jun. 30, 2008, 9 pages.
Final Office Action for U.S. Appl. No. 11/006,495, Mail Date: Mar. 20, 2009, 8 pages.
Non-Final Office Action for U.S. Appl. No. 11/006,495, Mail Date: Dec. 29, 2009, 9 pages.
Non-Final Office Action for U.S. Appl. No. 11/033,452, Mail Date: Dec. 11, 2008, 6 pages.
Non-Final Office Action for U.S. Appl. No. 11/033,452, Mail Date: Oct. 13, 2009, 7 pages.
Non-Final Office Action for U.S. Appl. No. 11/436,407, Mail Date: Jun. 12, 2009, 13 pages.
Non-Final Office Action for U.S. Appl. No. 11/362,366, Mail Date: Apr. 7, 2009, 6 pages.
Final Office Action for U.S. Appl. No. 11/436,407 mailed on April 5, 2010.
Non-Final Office Action for U.S. Appl. No. 11/436,407 mailed on October 29, 2010.
International Search Report for application No. PCT/US07/11597, Applicant: Vertiflex, Inc.; Mail Date Oct. 2, 2008, 2 pages.
International Preliminary Report on Patentability (mailed on Nov. 17, 2008) and Written Opinion (mailed on Oct. 2, 2008) for application No. PCT/US07/11597, Applicant: Vertiflex, Inc.; 6 pages.
International Preliminary Report on Patentability (mailed on Dec. 1, 2009) and Written Opinion (mailed on Dec. 19, 2008) for Application No. PCT/US2008/006598, pp. 5.
International Preliminary Report on Patentability (mailed on Mar. 24, 2010) and Written Opinion (mailed on Mar. 31, 2009) for Application No. PCT/US2008/076815, pp. 5.
International Preliminary Report on Patentability (issued on Aug. 10, 2010) and Written Opinion (mailed on Aug. 27, 2009) for application No. PCT/US09/033174, 5 pages.
International Preliminary Report on Patentability and Written Opinion for application No. PCT/US09/053740, Mail Date Mar. 24, 2010, 11 pages.

Requirement for Restriction/Election for U.S. Appl. No. 10/970,366 mailed on Apr. 3, 2008.
Non-Final Office Action for U.S. Appl. No. 10/970,366 mailed on Aug. 5, 2010.
Final Office Action for U.S. Appl. No. 11/006,495 mailed on Sep. 16, 2010.
Final Office Action for U.S. Appl. No. 11/033,452 mailed on Aug, 5, 2010
Examiner's First Report on Australian Patent Application No. 2005295209 mailed on Jun. 22, 2010. pp. 3.
European Supplementary Search Report for Application No. EP05816030; Applicant: Vertiflex, Inc.; Date Mail: Sep. 7, 2009. pp. 6.
Final Office Action for U.S. Appl. No. 11/362,366 mailed on Apr. 23, 2010 pp. 6.
International Search Report (mailed on Mar. 31, 2009) for Application No. PCT/US2008/076815, pp. 3.
International Search Report for application No. PCT/US09/033174, Mail Date Aug. 27, 2009), 2 pages.
International Search Report and Written Opinion for application No. PCT/US09/053740, Mail Date Mar. 24, 2010, 4 pages.
International Preliminary Report on Patentability (issued on Aug. 26, 2008) and Written Opinion (mailed on Jul. 8, 2008) for application No. PCT/US07/04726, 4 pages.
International Search Report (mailed on Jul. 8, 2008) for application No. PCT/US07/04726. pp. 1.
International Preliminary Report on Patentability (issued on Apr. 24, 2007) and Written Opinion (mailed on Apr. 10, 2008) for application No. PCT/US05/38021. pp. 4.
International Search Report (mailed on Apr. 10, 2006) for application No. PCT/US05/38021. pp. 1.
International Search Report (mailed on Dec. 19, 2008) for Application No. PCT/US2008/006598, pp. 2.
International Preliminary Report on Patentability (issued on Jan. 22, 2008) and Written Opinion (mailed on Jul. 27, 2007) for application No. PCT/US06/28586. pp. 9.
International Search Report (mailed on Jul. 27, 2007) for application No. PCT/US06/28586. pp. 2.
International Preliminary Report on Patentability (issued on Nov. 17, 2008) and Written Opinion (mailed on Apr. 23, 2008) for application No. PCT/US07/11573. pp. 4.
International Search Report (mailed on Apr. 23, 2008) for application No. PCT/US07/11573. pp. 1.
Final Office Action for U.S. Appl. No. 10/970,366 mailed on Jan. 13, 2011.
Advisory Action for U.S. Appl. No. 11/006,495 mailed on Dec. 30, 2010.
Non-Final Office Action for U.S. Appl. No. 11/033,452 mailed on Dec. 23, 2010.
Non-Final Office Action for U.S. Appl. No. 11/362,366 mailed on Mar. 18, 2011.

* cited by examiner (A)　　　　　　　　(B)

FIG. 12
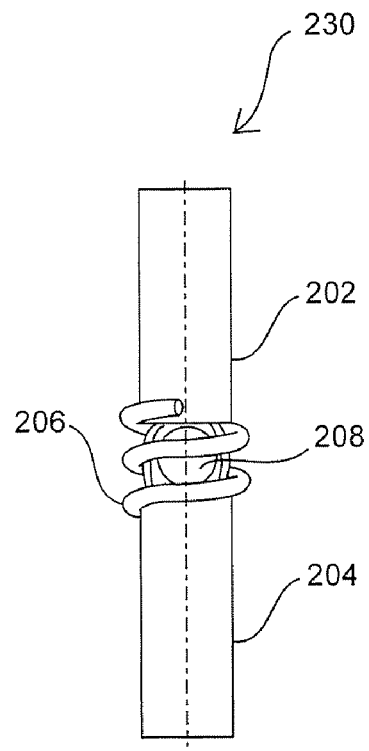
(A)
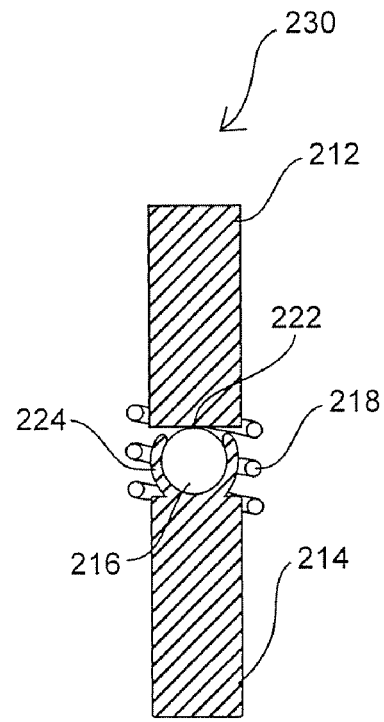
(B)
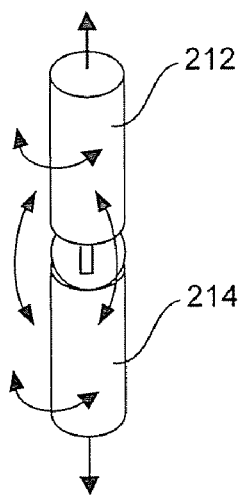
(C)
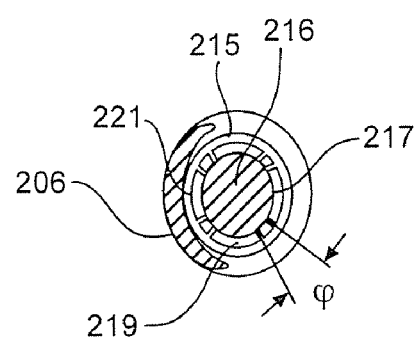
(D)

FIG. 16
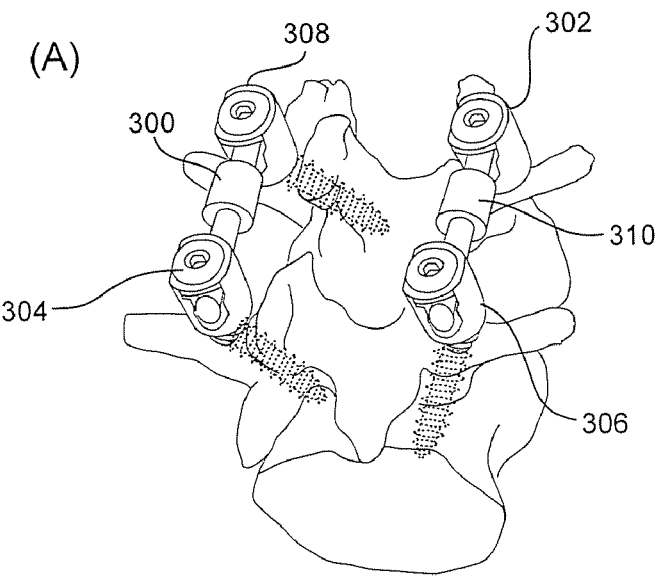
(A)
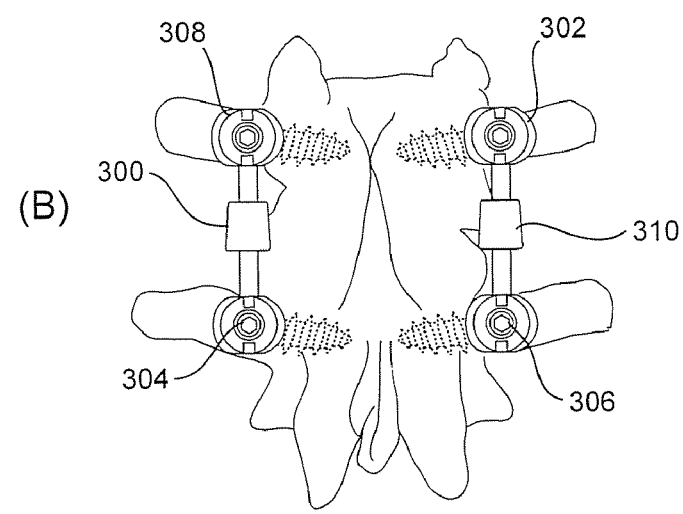
(B)
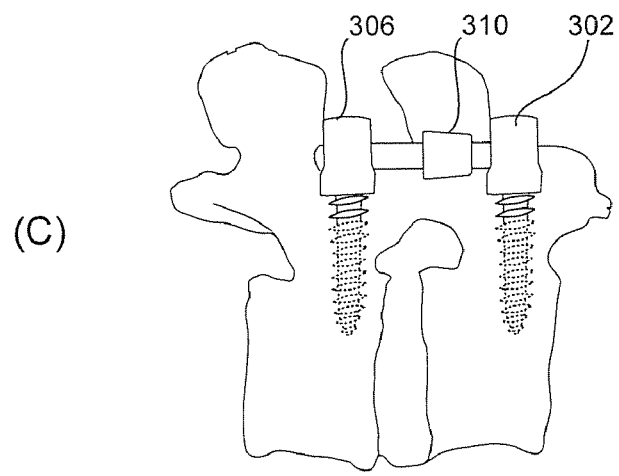
(C)

FIG. 17
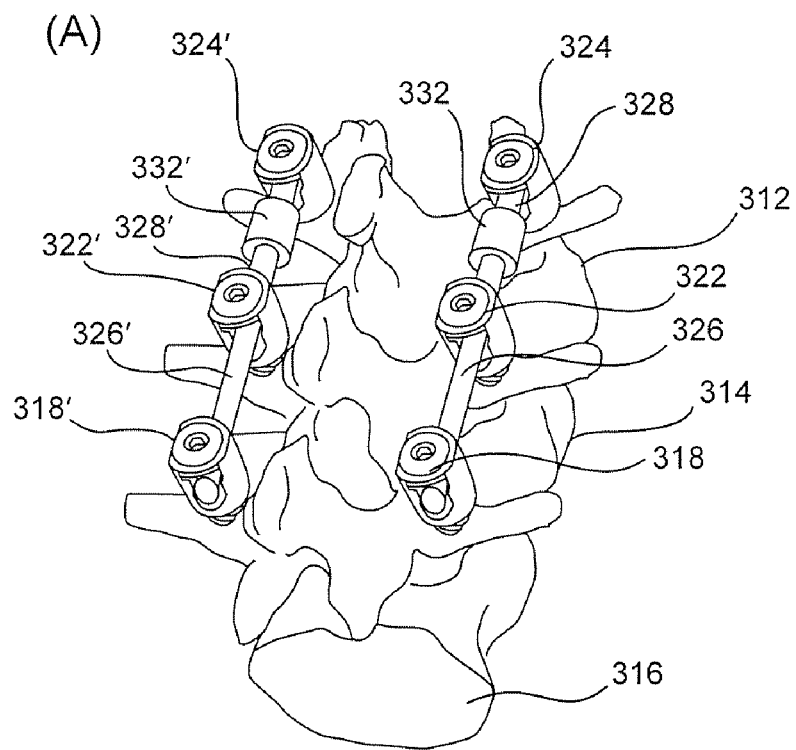
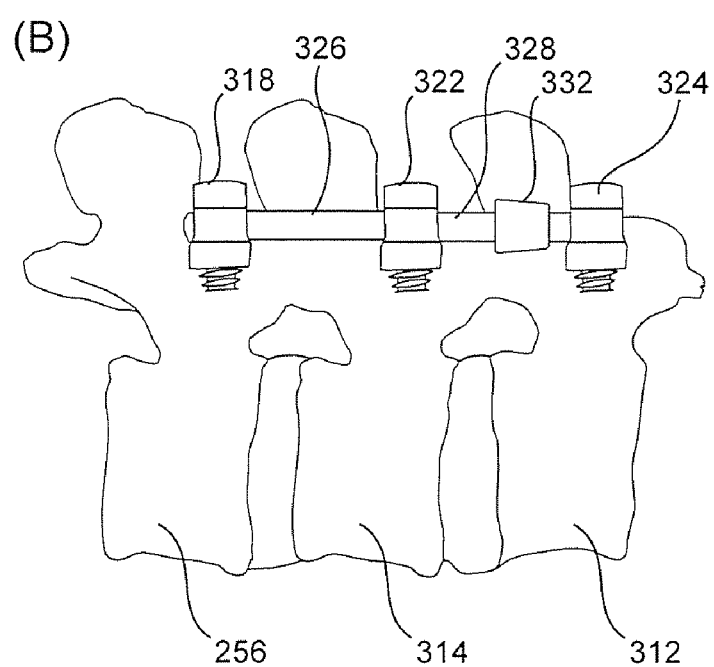

SYSTEMS AND METHODS FOR STABILIZATION OF BONE STRUCTURES

CROSS-REFERENCE

This application is a continuation-in-part of prior-filed U.S. Non-Provisional patent application Ser. No. 11/436,407, filed May 17, 2006, which is a continuation-in-part of U.S. Non-Provisional patent application Ser. No. 11/033,452 filed Jan. 10, 2005, which is a continuation-in-part of U.S. Non-Provisional patent application Ser. No. 11/006,495 filed Dec. 6, 2004, which is a continuation-in-part of U.S. Non-Provisional patent application Ser. No. 10/970,366, filed on Oct. 20, 2004; this application is also a continuation-in-part of prior-filed U.S. Non-Provisional patent application Ser. No. 11/362,366, filed Feb. 23, 2006, which is a continuation-in-part of U.S. Provisional Patent Application Ser. No. 60/701,660, filed Jul. 22, 2005, all of which are incorporated herein by reference in their entirety and are assigned to the assignee of the present invention.

FIELD OF THE INVENTION

The present invention is directed towards the treatment of spinal disorders and pain. More particularly, the present invention is directed to systems and methods of treating the spine, which eliminate pain and enable spinal motion, which effectively mimic that of a normally functioning spine.

BACKGROUND OF THE INVENTION

FIGS. 1A and 1B illustrate a portion of the human spine having a superior vertebra 2 and an inferior vertebra 4, with an intervertebral disc 6 located in between the two vertebral bodies. The superior vertebra 2 has superior facet joints 8a and 8b, inferior facet joints 10a and 10b, posterior arch 16 and spinous process 18. Pedicles 3a and 3b interconnect the respective superior facet joints 8a, 8b to the vertebral body 2. Extending laterally from superior facet joints 8a, 8b are transverse processes 7a and 7b, respectively. Extending between each inferior facet joint 10a and 10b and the spinous process 18 are lamina 5a and 5b, respectively. Similarly, inferior vertebra 4 has superior facet joints 12a and 12b, superior pedicles 9a and 9b, transverse processes 11a and 11b, inferior facet joints 14a and 14b, lamina 15a and 15b, posterior arch 20, spinous process 22.

The superior vertebra with its inferior facets, the inferior vertebra with its superior facets, the intervertebral disc, and seven spinal ligaments (not shown) extending between the superior and inferior vertebrae together comprise a spinal motion segment or functional spine unit. Each spinal motion segment enables motion along three orthogonal axes, both in rotation and in translation. The various spinal motions are illustrated in FIGS. 2A-2C. In particular, FIG. 2A illustrates flexion and extension motions and axial loading, FIG. 2B illustrates lateral bending motion and translation, and FIG. 2C illustrates axial rotational motion. A normally functioning spinal motion segment provides physiological limits and stiffness in each rotational and translational direction to create a stable and strong column structure to support physiological loads.

Traumatic, inflammatory, metabolic, synovial, neoplastic and degenerative disorders of the spine can produce debilitating pain that can affect a spinal motion segment's ability to properly function. The specific location or source of spinal pain is most often an affected intervertebral disc or facet joint, and in particular the nerves in and around the intervertebral disc or facet joint. Often, a disorder in one location or spinal component can lead to eventual deterioration or disorder, and ultimately, pain in another.

Spine fusion (arthrodesis) is a procedure in which two or more adjacent vertebral bodies are fused together once the natural height of the degenerated disc has been restored. It is one of the most common approaches to alleviating various types of spinal pain, particularly pain associated with one or more affected intervertebral discs. However, fusion is only as good as the ability to restore disc height to relieve the pain by taking pressure off the nerves, nerve roots, and/or articulating surfaces—i.e., facet joints and end plates of the vertebral bodies. While spine fusion generally helps to eliminate certain hypes of pain, it has been shown to decrease function by limiting the range of motion for patients in flexion, extension, rotation and lateral bending. Furthermore, fusion creates increased stresses on adjacent non-fused motion segments and accelerated degeneration of the motion segments. Additionally, pseudarthrosis (resulting from an incomplete or ineffective fusion) may not provide stability of the degenerative spine or the expected pain-relief for the patient. Also, the device(s) used for fusion, whether artificial or biological, may migrate out of the fusion site creating significant new problems for the patient. In addition, fusion of the spine causes the increased transfer of stresses to the anatomical structures above and below the site of fusion. The additional stresses may cause the accelerated degeneration of anatomical structures above and below the original site of fixation, thus necessitating further surgical intervention in order to arrest the degeneration of these levels, to restore stability of the degenerated spine, and to relieve the pain associated with this process.

Various technologies and approaches have been developed to treat spinal pain without fusion in order to maintain or recreate the natural biomechanics of the spine. To this end, significant efforts are being made in the use of implantable artificial intervertebral discs. Artificial discs are intended to replace the natural disc while restoring articulation between vertebral bodies so as to recreate the full range of motion normally allowed by the elastic properties of the natural disc. Unfortunately, the currently available artificial discs do not adequately address all of the mechanics of motion for the spinal column.

Most recently, surgical-based technologies, referred to as "dynamic posterior stabilization," have been developed to address spinal pain resulting from more than one disorder, when more than one structure of the spine have been compromised. An objective of such technologies is to provide the support of fusion-based implants while restoring the natural biomechanics of the spine. This approach helps reduce the amount of stress transmitted or shifted to the level above or below that which is being treated to reduce the acceleration of the degenerative process typically seen in rigid devices used to fuse the spine. Dynamic posterior stabilization systems typically fall into one of three general categories: (1) interspinous spacers (2) posterior pedicle screw-based systems and (3) facet arthroplasty systems.

Examples of interspinous spacers are disclosed in U.S. Pat. Nos. Re. 36,211, 5,645,599, 6,695,842, 6,716,245 and 6,761,720. The spacers, which are made of either a hard or compliant material, are placed between adjacent spinous processes. Because the interspinous spacers involve attachment to the spinous processes, use of these types of systems is limited to applications where the spinous processes are uncompromised and healthy.

Examples of pedicle screw-based systems are disclosed in U.S. Pat. Nos. 5,015,247, 5,484,437, 5,489,308, 5,609,636 and 5,658,337, 5,741,253, 6,080,155, 6,096,038, 6,264,656 and 6,270,498. These types of systems involve the use of screws which are positioned in the vertebral body through the pedicle. Certain types of these pedicle screw-based systems may be used to augment compromised facet joints, while others require removal of the spinous process and/or the facet joints for implantation. One such system, the Zimmer Spine Dynesys® employs a cord which is extended between the pedicle screws and a fairly rigid spacer which is passed over the cord and positioned between the screws. While this system is able to provide load sharing and restoration of disc height, because it is so rigid, it is not effective in preserving the natural motion of the spinal segment into which it is implanted. Other pedicle screw-based systems employ articulating joints between the vertebral bodies which are intended to replace the facet joints, and are anchored to the veterbral bodies via the pedicle screws.

With the limitations of current spine stabilization technologies, there is clearly a need for an improved means and method for dynamic posterior stabilization of the spine which address the drawbacks of prior devices. In particular, it would be highly beneficial to have a dynamic stabilization system that enables the spine to mimic the motion of one or more healthy, uncompromised vertebral segments without limiting natural extension/flexion, axial rotational, and lateral bending movements. It would be additionally beneficial if such a system could be used to treat all spinal indications regardless of pain source, prevent or slow the deterioration of the intervertebral discs, or even restore disc height, and be used in conjunction with prosthetic intervertebral discs.

SUMMARY OF THE INVENTION

The current invention provides an enhanced dynamic rod system that may be disposed between two pedicle screws, two crossbars, a combination of a pedicle screw and a crossbar, or two other spinal devices, that can provide a patient with spinal support and freedom of movement that is very close to that of a normally-functioning healthy spine. The dynamic nature allows controlled flexibility, motion, and movement, between two vertebral segments being stabilized. A high degree of the natural biomechanics and motion are preserved. In addition, pain is reduced and long-term complications are reduced. The system also avoids unnecessary stresses placed on neighboring vertebral segments, as are seen in standard fusion techniques, which cause accelerated degeneration of vertebral structures and associated pain.

Embodiments of the system may include two rod segments that are joined by a dynamic element. The dynamic element may include flexible materials, flexible assemblies such as threaded sections joined by springs, elastomeric materials, and other such components as are described below.

The current invention is applicable to patients with degenerative disc disease, spinal stenosis, severe spondylolisthesis at L5-S1, spinal deformities, fractures, pseudarthrosis, tumors, failed prior fusions, or other similar vertebral segment traumas and diseases.

The current invention allows convenient installation and removal in a patient. The ease of installation and removal in turn allows embodiments to be removed if further degeneration occurs, to be replaced with a fixed rod installed into the bone screws already installed in the pedicles. This allows the surgeon a revision strategy for the patient between the different systems.

Advantages of the invention may include one or more of the following. A semi-rigid rod system is provided which mimics the natural biomechanics of the spinal segment. Motion and movement are allowed, e.g., 1.0 mm extension, 5° angular flexion, and 15° torsional deflection. Embodiments of the system allow for offset and offloading of affected anatomical structures undergoing degenerative changes. The spring design may bias the spine back to a neutral position.

Other advantages will be apparent from the description that follows, including the figures and claims.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 12(A)-(D) illustrate side, sectional, perspective, and top views of a dynamic rod system according to yet another embodiment of the current invention.

FIG. 16(A)-(C) illustrate views of a dynamic rod system according to an embodiment of the current invention in use as installed in a set of vertebral segments.

FIGS. 17(A) and 17(B) illustrate views of a multi-level dynamic rod system according to an embodiment of the current invention in use as installed in a set of vertebral segments.

DETAILED DESCRIPTION OF THE INVENTION

Before the present invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a rod" includes a plurality of such rods and reference to "the spring" includes reference to one or more springs and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1A:
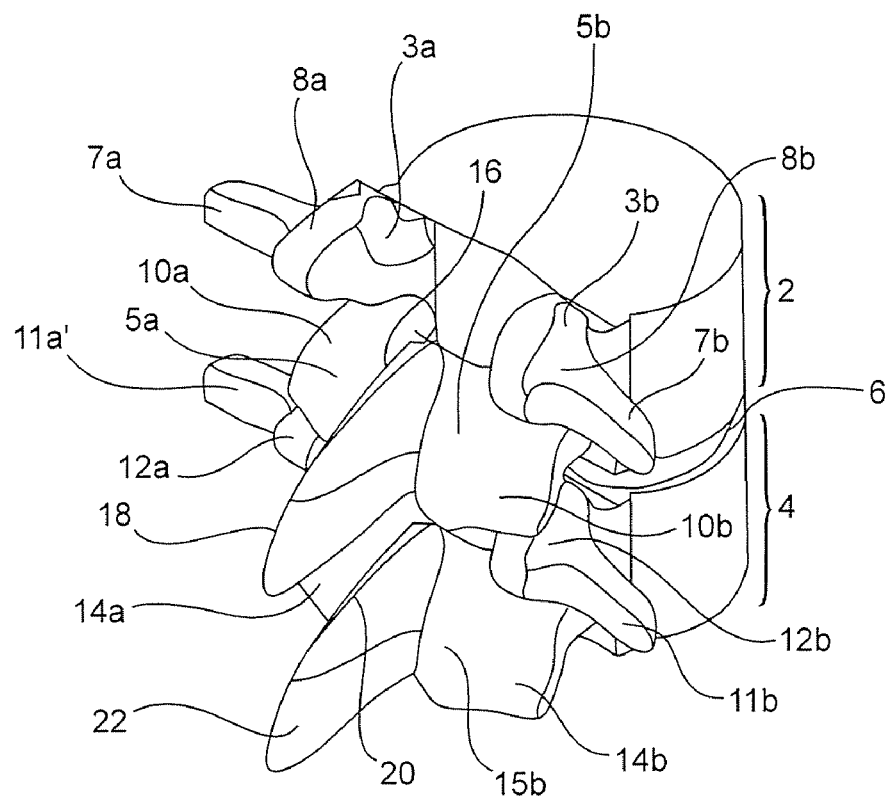
FIGS. 1(A) and 1(B) illustrate perspective views of a portion of the human spine having two vertebral segments, where the spinous process and the lamina of the superior vertebra have been resected in FIG. 1(B).
Figure 1B:
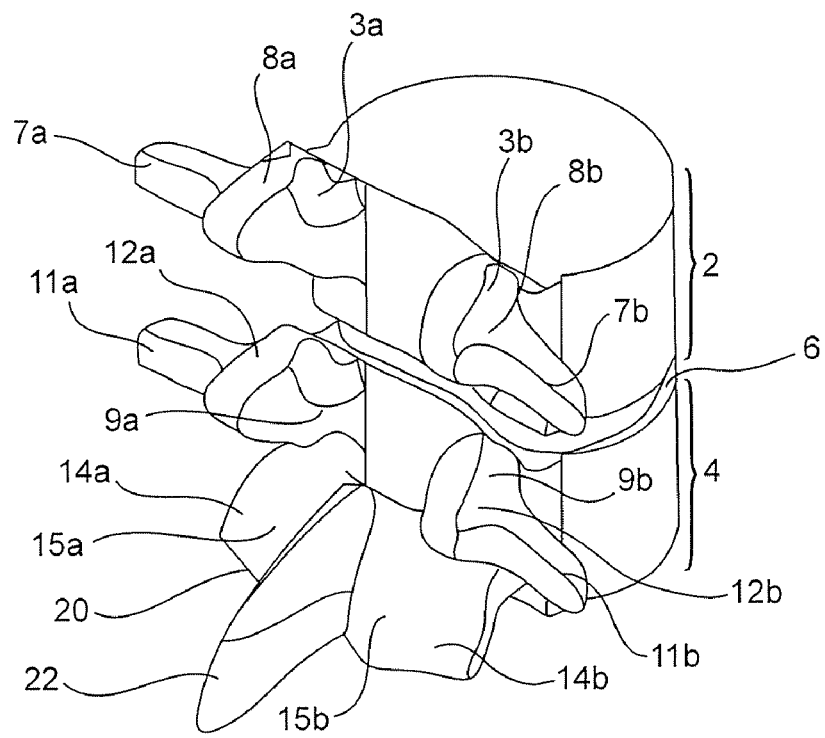
Figure 2A:
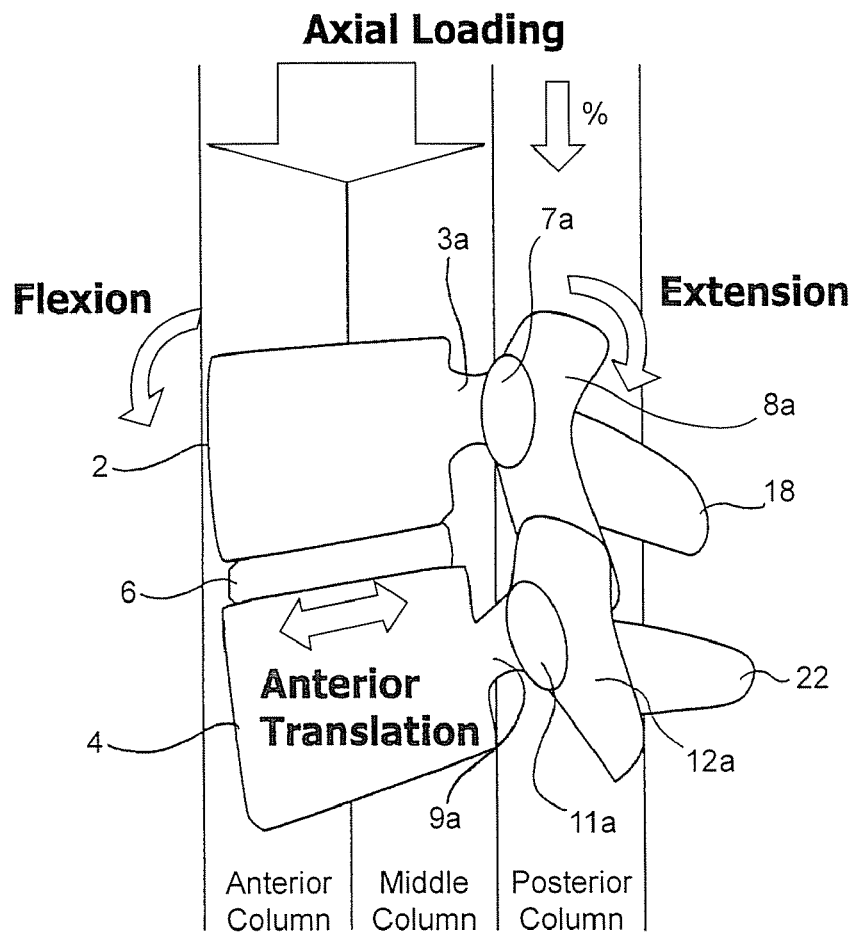
FIGS. 2(A)-(C) illustrate left side, dorsal and top views, respectively, of the spinal segments of FIG. 1(A) under going various motions.
Figure 2B:
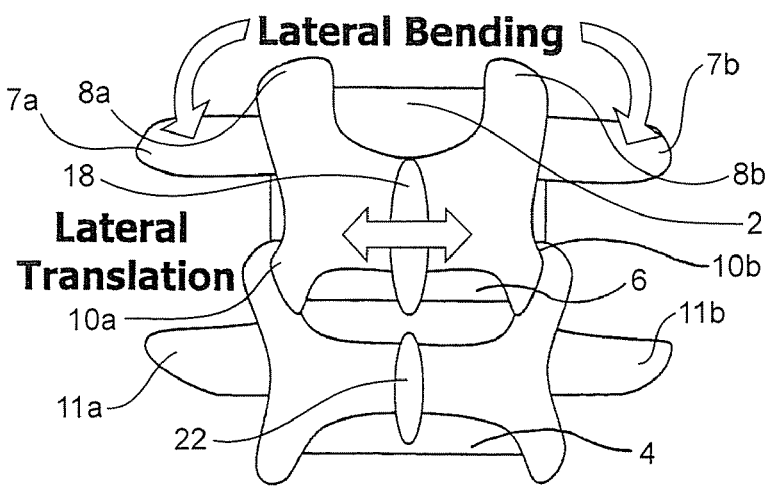
Figure 2C:
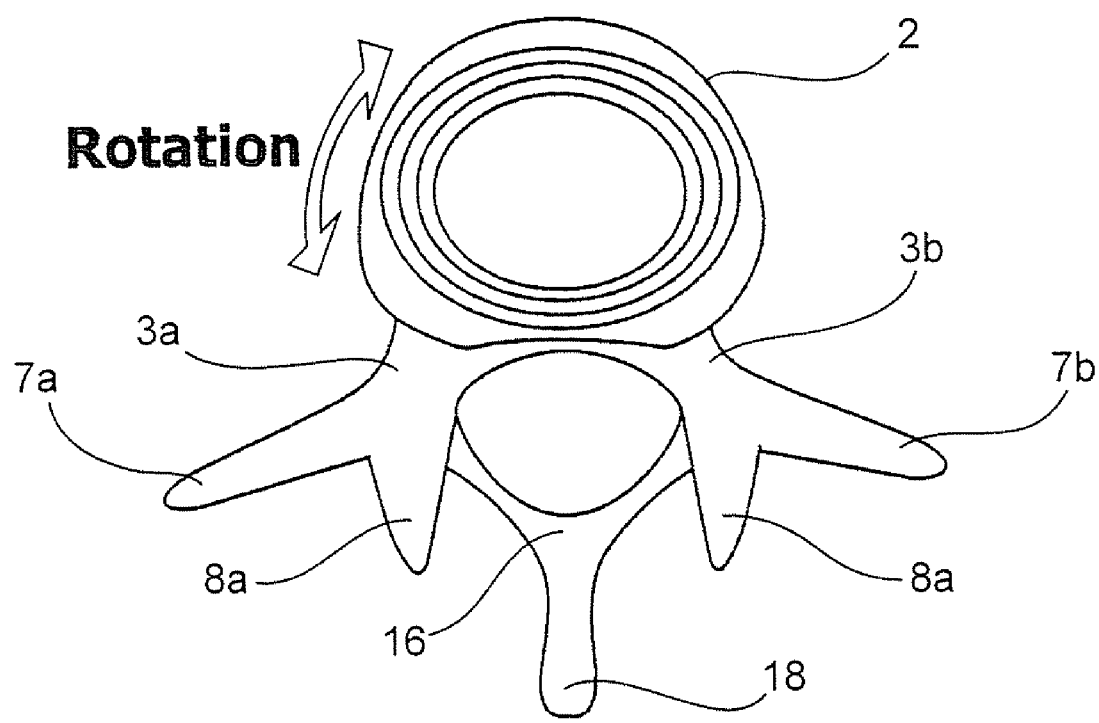

The present invention will now be described in greater detail by way of the following description of exemplary embodiments and variations of the systems and methods of the present invention. While more fully described in the context of the description of the subject methods of implanting the subject systems, it should be initially noted that in certain applications where the natural facet joints are compromised, as illustrated in FIG. 1(B), inferior facets 10a and 10b, lamina 5a and 5b, posterior arch 16 and spinous process 18 of superior vertebra 2 of FIG. 1(A) may be resected for purposes of implantation of certain of the dynamic stabilization systems of the present invention. In other applications, where possible, the natural facet joints, lamina and/or spinous processes are spared and left intact for implantation of other dynamic stabilization systems of the present invention.

It should also be understood that the term "system", when referring to a system of the present invention, most typically refers to a set of components which includes multiple bone stabilization components such as a superior, cephalad or rostral (towards the head) component configured for implantation into a superior vertebra of a vertebral motion segment and an inferior or caudal (towards the feet) component configured for implantation into an inferior vertebra of a vertebral motion segment. A pair of such component sets may include one set of components configured for implantation into and stabilization of the left side of a vertebral segment and another set configured for the implantation into and stabilization of the right side of a vertebral segment. Where multiple bone segments such as spinal segments or units are being treated, the term "system" may refer to two or more pairs of component sets. i.e. two or more left sets and/or two or more right sets of components. Such a multilevel system involves stacking of component sets in which each set includes a superior component, an inferior component, and one or more medial components therebetween.

The superior and inferior components (and any medial components therebetween), when operatively implanted, may be engaged or interface with each other in a manner that enables the treated spinal motion segment to mimic the function and movement of a healthy segment, or may simply fuse the segments such as to eliminate pain and/or promote or enhance healing. The interconnecting or interface means include one or more structures or members that enables, limits and/or otherwise selectively controls spinal or other body motion. The structures may perform such functions by exerting various forces on the system components, and thus on the target vertebrae. The manner of coupling, interfacing, engagement or interconnection between the subject system components may involve compression, distraction, rotation or torsion, or a combination thereof. In certain embodiments, the extent or degree of these forces or motions between the components may be intraoperatively selected and/or adjusted to address the condition being treated, to accommodate the particular spinal anatomy into which the system is implanted, and to achieve the desired therapeutic result.

In certain embodiments, the multiple components, such as superior and inferior spinal components, are mechanically coupled to each other by one or more interconnecting or interfacing means. In other embodiments, components interface in an engaging manner, which does not necessary mechanically couple or fix the components together, but rather constrains their relative movement and enables the treated segment to mimic the function and movement of a healthy segment. Typically, spinal interconnecting means is a dorsally positioned component, i.e., positioned posteriorly of the superior and inferior components, or may be a laterally positioned component, i.e., positioned to the outer side of the posterior and inferior components. The structures may involve one or more struts and/or joints that provide for stabilized spinal motion.

Reference will now be made in detail to the present embodiments of the invention, examples of which are illustrated in the accompanying drawings. Wherever possible, the same reference numbers will be used throughout the drawings to refer to the same or like parts.

Figure 3A:
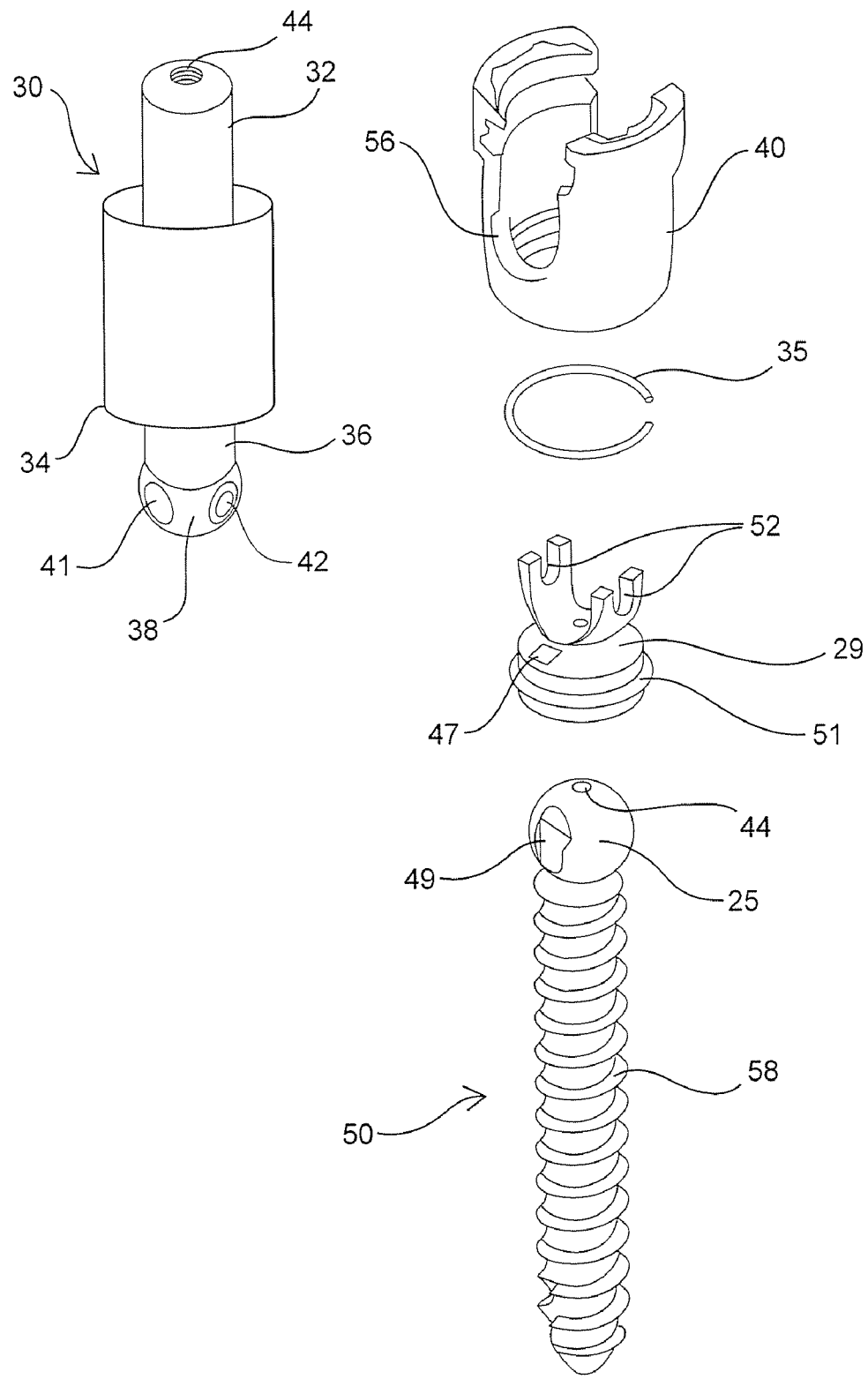
FIG. 3(A)-(B) illustrate exploded, combined, and rotated perspective views of a pedicle screw and dynamic rod combination, where the dynamic rod can be rotated to assume a variety of angles relative to the pedicle screw.
Figure 3B:
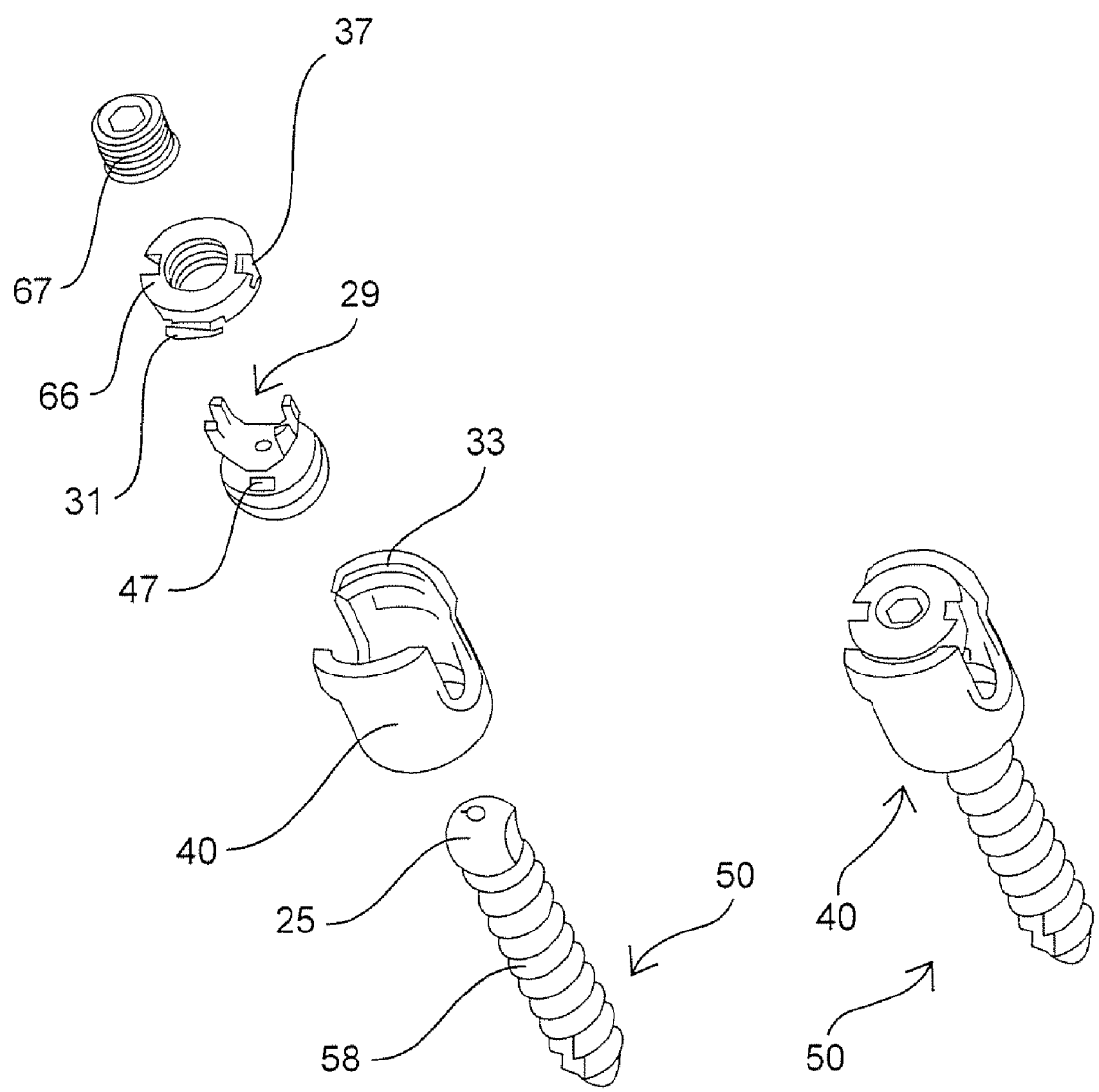

Referring to FIGS. 3(A) and 3(B), there is illustrated a bone stabilization device according to an embodiment of the invention. The device includes a dynamic rod 30, a seat 40, and a bone screw 50. Certain aspects of the bone screw and seat are described here; however, a more complete description of these components may be found in the applications incorporated by reference above. The dynamic rod may be employed with any such bone screw systems, or indeed with components coupled to bone screw systems through intervening or intermediary devices.

The dynamic rod 30 includes a sleeve cap 34. The sleeve cap 34 is generally cylindrical or conical in shape, although other shapes can also be accommodated. The dynamic rod has a distal shaft 32 which is defined to be distal of the sleeve cap 34 relative to a pivot point on the opposite side of the rod. The dynamic rod 30 also has a proximal shaft 36 which terminates in a ball end 38 having a flat portion on which is mounted a pin 42. Pin 42 has a matching pin (not shown) on the opposite side of the ball end 38. In certain embodiments, the dynamic rod has a cannula 44 disposed centrally therethrough.

A bone anchoring portion includes a seat 40 and a bone screw 50. The cannula 44 may pass through dynamic rod 30 and through the bone anchoring portion such that the assembly may be passed, in the orientation shown in the figure, into a patient through a installation cannula (not shown) and over a previously-placed guidewire, such as a "K-wire" commonly used in bone and joint procedures. However, in many cases, no such cannula, lumen, or guidewire is necessary for placement.

As noted above, at one end of dynamic rod 30 is ball end 38, which is rotationally received and captured by a coupler 29. In particular, U-shaped grooves 52 are provided which mate with the corresponding pins 42 on dynamic rod 30 to allow the dynamic rod 30 to be pivoted in a perpendicular (or other angular) fashion relative to the rest of the system. The coupler 29 may be attached to the seat 40 via a retaining ring having lugs which cooperatively and securely engage corresponding slots in the coupler 29 (and may also engage slots in the seat 40). The retaining ring may be secured to the seat 40 via a groove formed in the cylindrical interior of the seat. In this way, the retaining ring and the coupler are press fit together into the seat. The coupler and seat have a keyway (not shown) such that they are aligned with one another. In this way, the coupler is prevented from being misaligned with the seat.

In an alternative embodiment, the "U"-shaped grooves may be replaced with a "closed" saddle having receivers. In this case, during installation of the dynamic rod, the pins on the dynamic rod push on ramps until the pins drop into holes. Once the pins drop they are captured and generally require a tool for removal. In this way, the end of the dynamic rod cannot be displaced when the opposite end of the dynamic rod is being captured by a receiving assembly. In this embodiment, the dynamic rod is not attached to the coupler prior to installation. Because of this, the bone screw can be driven directly through a hole in the coupler, and no tangential rotation arrangement is necessary.

Returning to the embodiment of FIGS. 3(A) and 3(B), the coupler mates with the ball end in a snap-fit ball-and-socket arrangement. The screw—ball end—coupler system sits within the seat and is at least partially secured therein because coupler lip 51 rests on seat lip 56. The screw—ball end—coupler system may be further secured using retaining ring 35 on top of lip 51 and press fit into seat lip 56.

The dynamic rod can be inserted into the saddle of the coupler, which is assembled to the seat, by an operator, or may be provided in a pre-attached state. The dynamic rod can be removable from the coupler, which is assembled to the seat, or may be permanently, though rotatably, attached, whether provided in a "to-be-assembled" or a pre-assembled state. The ball and socket design of FIGS. 3(A) and 3(B) allows multidirectional rotation of the dynamic rod 30. Alternative designs may allow a single degree of freedom, or may allow more sophisticated trajectories of travel for the dynamic rod 30.

After the dynamic rod has been pivoted to a position for use in a patient, the dynamic rod may be held in that position by use of the closure element or cap 66 and a set screw 67. The closure element 66 may be snap-fitted into the seat 40 by interaction and engagement of closure element tabs 31 and seat grooves 33. Instead of grooves and tabs, lugs may also be employed. Lugs have the benefit of preventing the seat 40 splaying and releasing the rod. Furthermore, besides the snap-fit of closure element 66, the same may also be dropped in and captured with set screws or other capture devices. One particular other such capture device includes an integral locking nut/plug combination, which eliminates the need for a plug and set screw set.

A closure element slot 37 may be disposed in the closure element 66 so that the same may be further tightened along the groove 33 if the groove 33 is provided with a ramp system. Of course, various other techniques may also be used to keep closure element 66 within seat 40. The set screw 67 may then be tightened to secure the dynamic rod 30 against movement.

In one method of use, the screw 50, the coupler 29, the seat 40, the rod 30, and the corresponding intermediate elements, are assembled prior to implantation in the patient. The device is inserted over the guidewire. The screw is then driven into the desired bone by use of a driver (not shown). In another method of use, the screw 50, the coupler 29, the seat 40, and the corresponding intermediate elements, are assembled prior to implantation in the patient. The screw is driven into the desired bone by use of a driver which cooperatively engages with a mating recess in the screw. Once the screw is driven into the bone, the dynamic rod is inserted, captured, and then may be pivoted and the closure element 66 and set screw 67 applied.

Figure 4:
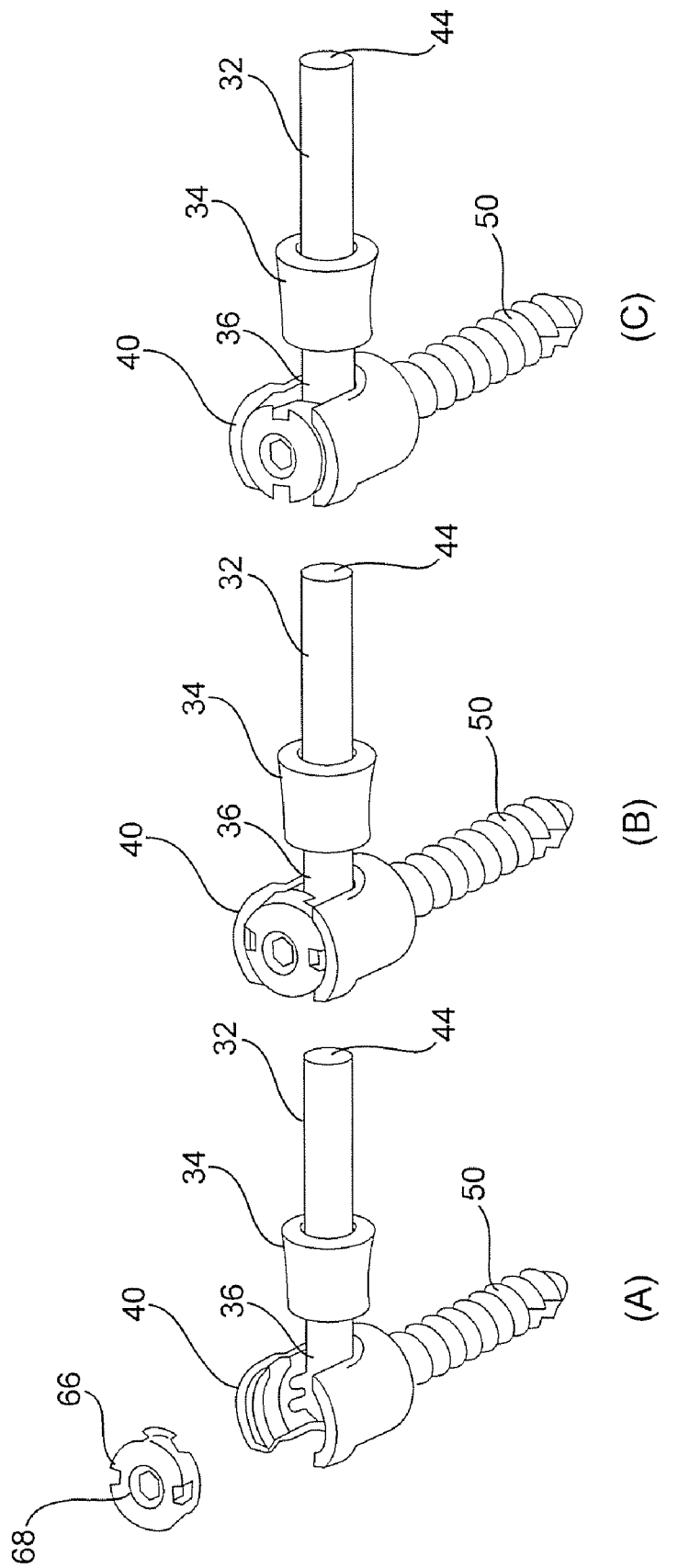
FIG. 4(A)-(C) illustrate exploded, combined, and locked views of a pedicle screw and dynamic rod combination, which the dynamic rod can be locked in place with a cap.

FIG. 4(A)-(C) show the system where the dynamic rod is pivoted, and the closure element is about to be disposed within the seat (4(A)). Similar reference numerals and parts refer to similar numerals and parts in FIGS. 3(A)-3(B). After pivoting, the closure element is disposed within the seat (4(B)). Finally, the closure element is tightened along with the set screw (4(C)).

Figure 5:
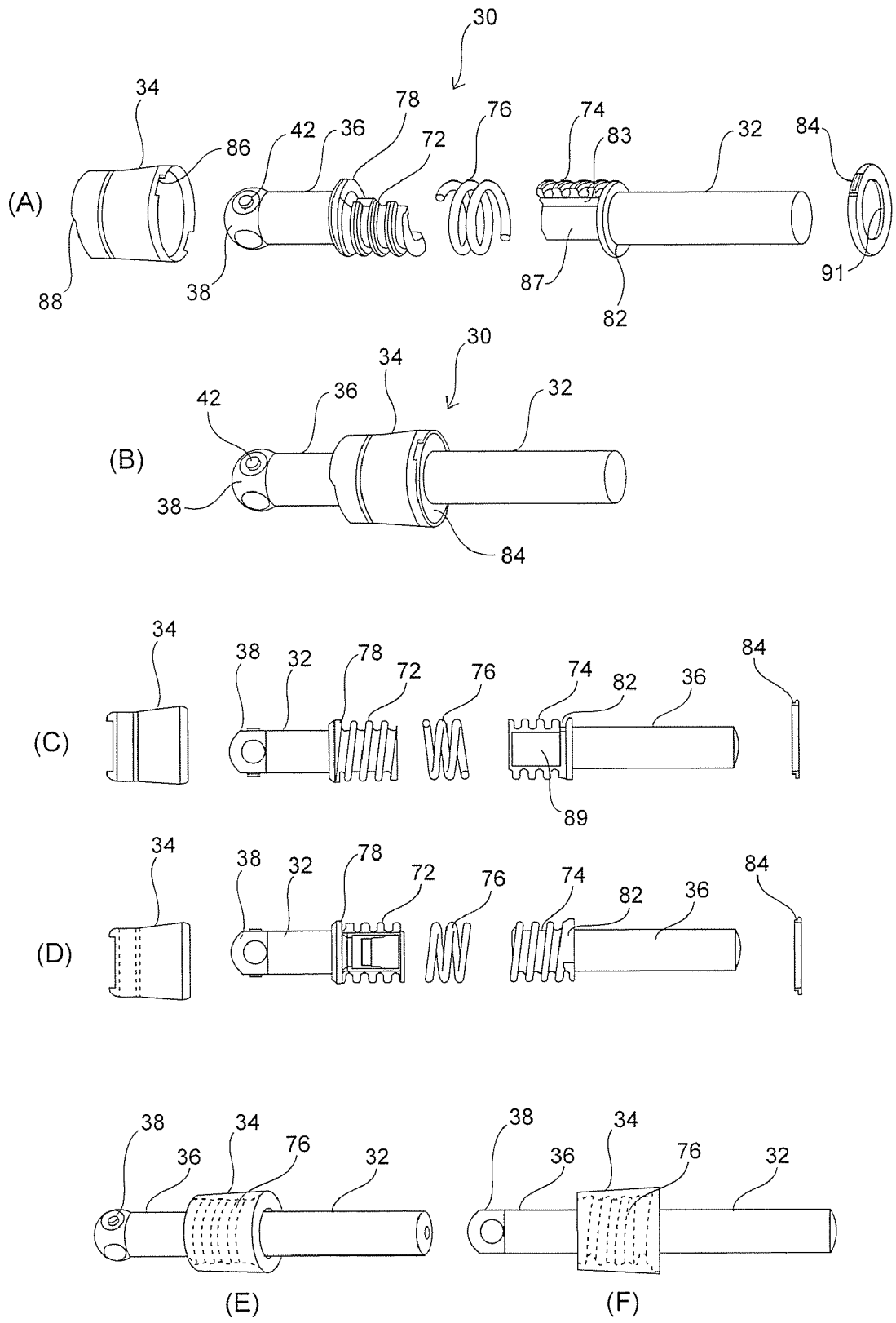
FIG. 5(A)-(F) illustrate exploded, combined, side, perspective transparent, and side transparent views of a dynamic rod system according to an embodiment of the current invention.

Referring to FIGS. 5(A) and 5(B), a first embodiment of a dynamic rod system is shown. The ball end 38 having pins 42 is shown at one end of a proximal rod segment 36, which terminates at its opposite end in a flange 78. Similarly, a distal rod segment 32 is shown which terminates at one end in flange 82. Flanges 82 and 78 each have one or more radially extending arc sections 83 and 85, respectively, which matingly engage one or more corresponding radially retracted arc sections 86 and 88, respectively, in a sleeve cap 34. A press-fit retaining end cap 84 can further be used to seal the sleeve cap 34. The end cap 84 may be made slightly oval in shape. In this way, it may control the direction in which flexion can occur. To ensure that the surgeon can distinguish this slight oval character, i.e., this marker, a line 91 may be etched on the assembly, here shown on the end cap, so that the surgeon is made aware of which direction preferred flexion will occur.

The sleeve cap and the end cap may be welded together to contain the system but may also still employ a slight gap between the end cap and the flange 82 to allow for an extension motion. Moreover, the sleeve cap 34 is shown with a frusto-conical shape in order to accommodate and limit angular flexion of the dynamic rod from end-to-end. Besides welding, the two may be press-fit, employ another type of mating snap feature or be attached with an adhesive. The sleeve cap and the end cap may each have an opening in which to slidingly receive their corresponding proximal or distal segments.

Disposed within sleeve cap 34 are the components that provide the dynamic movement. In particular, a proximal threaded section 72 is provided at a distal end of proximal rod segment 36, and a distal threaded section 74 is provided at a proximal end of distal rod segment 32. In construction, the proximal and distal threaded sections are complementary in that they are disposed as shown to together form most of a complete and continuous thread; however, in most embodiments, they do not form the complete thread. Two, three, or more grooves may form this thread on each segment. In any case, rather than forming a complete 360° thread, they form a thread with one or more gaps of, e.g., 15° each. Of course, numerous other values may be employed as dictated by the requirements of the patient. Each of the proximal and distal end sections may be further optionally supported by a cylindrical core, one of which is shown in FIG. 5(A) as cylindrical core 87. The cylindrical cores provide strength to the threaded sections, and further provide a convenient guide or marker to be used during manufacturing, i.e., to indicate a pre-set position prior to conjunction with a spring. In general, the distal rod segment 32 may be provided with a cylindrical core 87 and the proximal rod segment 36 is provided with a smaller cylindrical core, i.e., one that provides a degree of support or strength, but otherwise the remaining interior of proximal threaded section 72 is left as void 89 (see also FIG. 5(C)). The void 89 may be cylindrical in shape but is generally frusto-conical to allow for, and limit, angular flexion of the cylindrical core 87 within the void 89.

The size of the cylindrical cores defines the maximum amount of compression afforded by the device, and the size of the housing defines the maximum amount of extension afforded by the device. In certain embodiment, the housing may be filled or partially filled with a resilient material, such as a silicone elastomer, to dampen motion and/or limit travel.

In more detail, the proximal and distal threaded sections are held together by a spring 76, which helically engages each of the proximal and distal threaded sections. The sleeve cap 34 covers the spring 76 and the proximal and distal threaded sections, in part to prevent blood and tissue in the spinal area from deleteriously affecting the dynamic mechanism.

In general, the spring may be configured to bias the system back to the neutral position. The spring controls rotation, flexion, and extension, and biases the system to a neutral or equilibrium position. In certain embodiments, the pitch of the spring may be greater or less than that of the proximal and distal threaded sections. In this way, the spring may be biased to push the two components together. In other embodiments, the pitch may be the same but the diameter of the wire of the spring may be smaller than the corresponding helical groove in which it sits to allow for torsion.

In some embodiments, a small gap may still be provided, e.g., 1.0 mm, to allow the components to extend.

FIGS. 5(D) and 5(E) show perspective and side transparent combined views of the dynamic rod of FIGS. 5(A)-(C).

Figure 6:
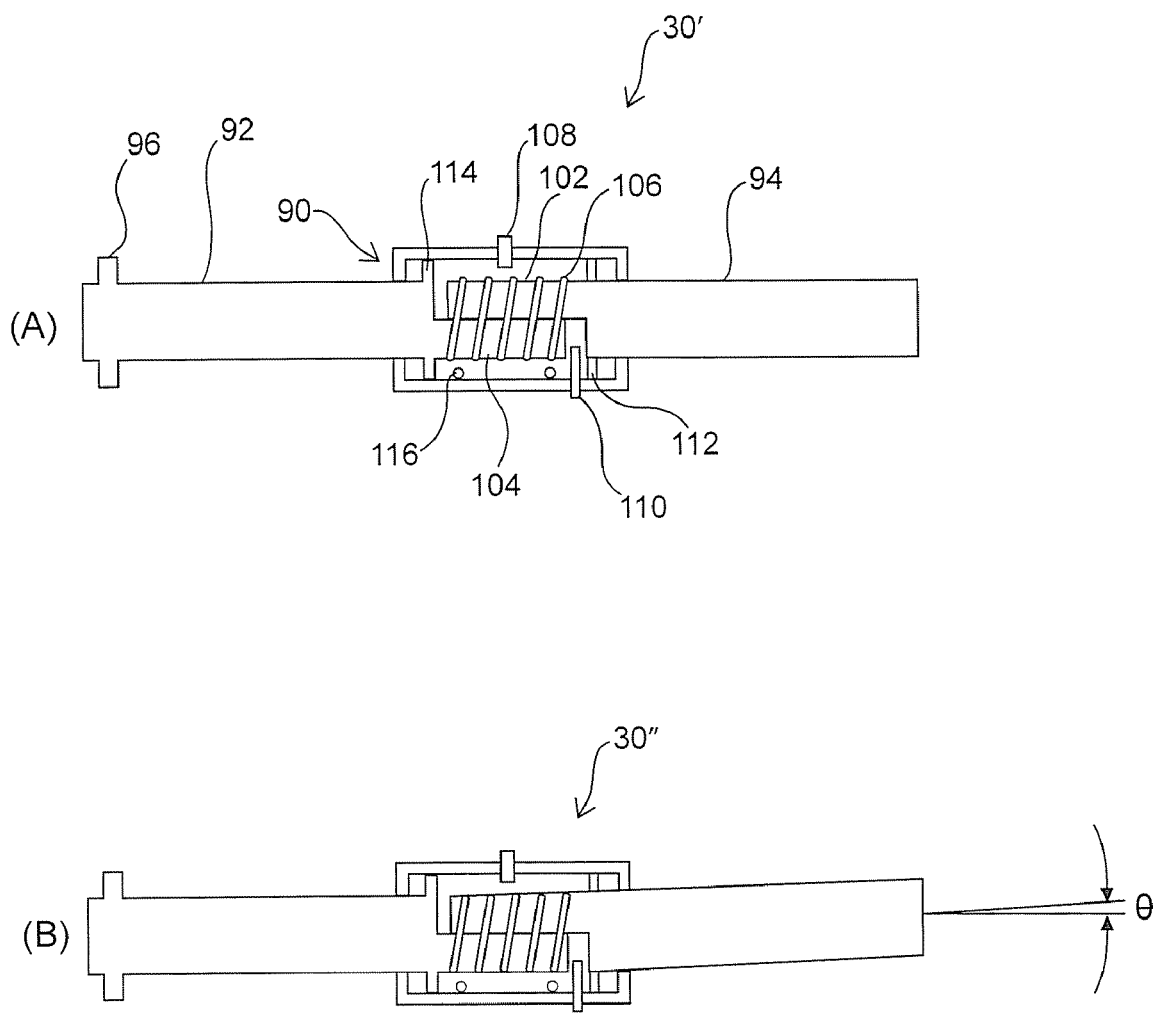
FIGS. 6(A) and 6(B) illustrate side sectional views of a dynamic rod system according to another embodiment of the current invention.

FIG. 6 shows an alternate embodiment of a dynamic rod system 30' according to the current invention. The dynamic rod system includes a dynamic element 90, a proximal rod segment 92, and a distal rod segment 94. Many of the features of the dynamic rod system 30' can be similar to corresponding elements in the dynamic rod system 30 of FIG. 5.

In the embodiment of FIG. 6, the dynamic rod system 30' employs hinge pins 96 which matingly engage elements such as the "U"-shaped grooves of FIG. 3. As in FIG. 5, the proximal segment has a distal end 104 and the distal segment has a proximal end 102. The distal end 104 and the proximal end 102 are joined by a spring 106. Flanges 112 and 114 serves similar purposes to the corresponding flanges in the embodiment of FIG. 5, to wit, sealing the housing and preventing removal of the elements of the dynamic rod system from the housing 98. Radioactive seeds 116 may be employed to assist in the prevention of undesired bone fusion.

In the embodiment of FIG. 6, various elements are provided to control certain adjustable ranges of motion for the dynamic rod 30'. For example, a set screw 108 may be provided to control the degree of angular flexion achievable by the dynamic rod system 30'. A set screw 110 may be provided to adjust the limits of extension and compression, and such set screws may be adjusted pre-, during-, or post-implantation. Finally, the housing 98 may be optionally filled with a material, such as an elastomer, to control the overall degree of dynamic response of the dynamic rod system 30'. For example, the elastomeric filling may be employed to improve the restoring force of the dynamic rod system. Similarly, the same may be employed to provide a dampening force. As with the housing or sleeve cap per se, the filling prevents contamination from entering the housing and also keeps debris from wear within the housing.

In the embodiment of FIG. 6(B), the elements of FIG. 6(A) are essentially reproduced. However, in FIG. 6(B), the proximal and distal rod segments of dynamic rod system 30" are not collinear. Rather, they are configured such that in an equilibrium position they mimic the curvature of the spine. In other words, they are not collinear but meet at an angle that is substantially the same as the curve the spinal axis takes in the local setting of the affected vertebral segments. This angle may be, e.g., 5 degrees. Other values may be employed according to the dictates of the patient.

Figure 7:
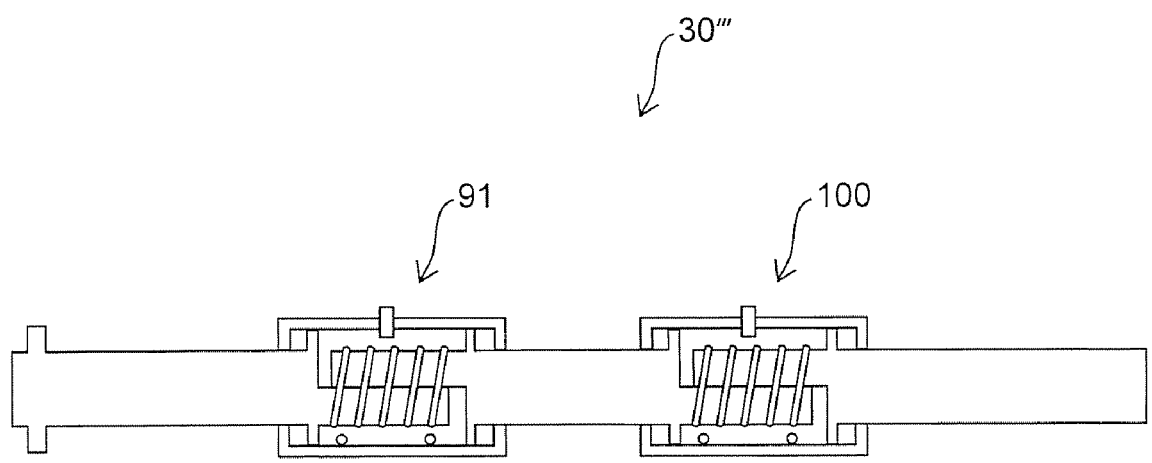
FIG. 7 illustrates a side sectional view of a dynamic rod system according to a further embodiment of the current invention.

Referring to FIG. 7, a further embodiment of a dynamic rod system 30'" is shown. The system 30'" has essentially similar elements to the embodiment of FIG. 6(A), and thus individual reference numerals are omitted. However, the system 30'" employs two dynamic elements 91 and 100. Elements 91 and 100 may be the same or dissimilar. The elements may be equidistantly arranged on the rod or may be arbitrarily placed to accommodate particular types of motion.

Figure 8:
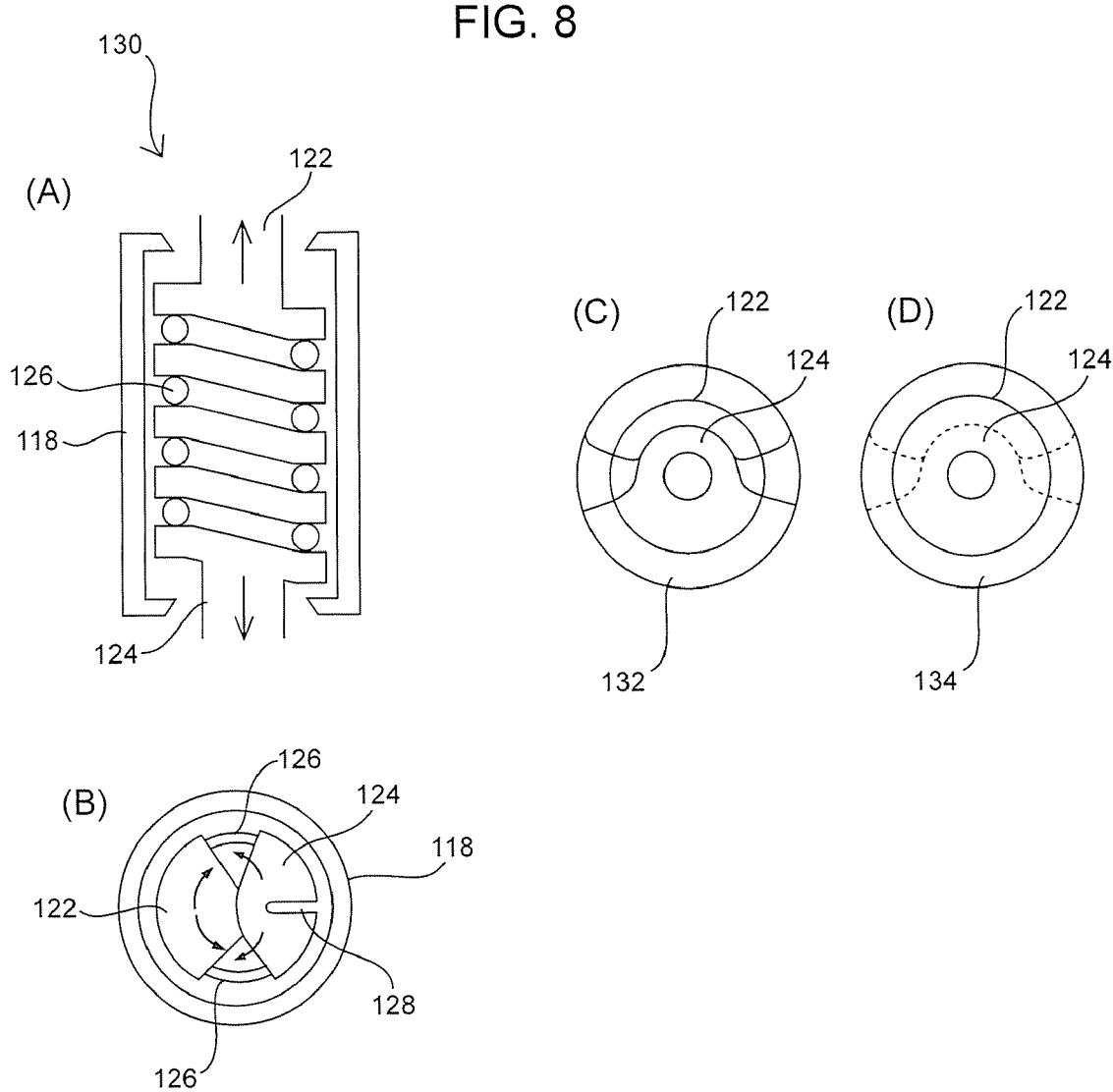
FIG. 8(A)-(D) illustrate side and top sectional views of a dynamic rod system according to yet another embodiment of the current invention.

Referring to FIG. 8(A), a further embodiment of a dynamic rod system 130 is shown. Many components are similar to the embodiment of FIG. 6(A). A proximal segment 122 is coupled to a distal segment 124 via a spring 126. In this embodiment, the housing 118 has flared walls to accommodate, and limit, additional flexion. Referring to the bottom view of FIG. 8(B), a spring end 128 may be fixed into one of the segments, here shown as the distal segment 124, via welding, adhesives, etc. Referring to FIG. 8(C), a round spring 132 may be employed, in which case all azimuthal angles may be provided with the same degree of flexion. On the other hand, referring to FIG. 8(D), an oval spring 134 may be employed, in which case certain azimuthal angles are preferred in terms of how much flexion they are allowed.

Figure 9:
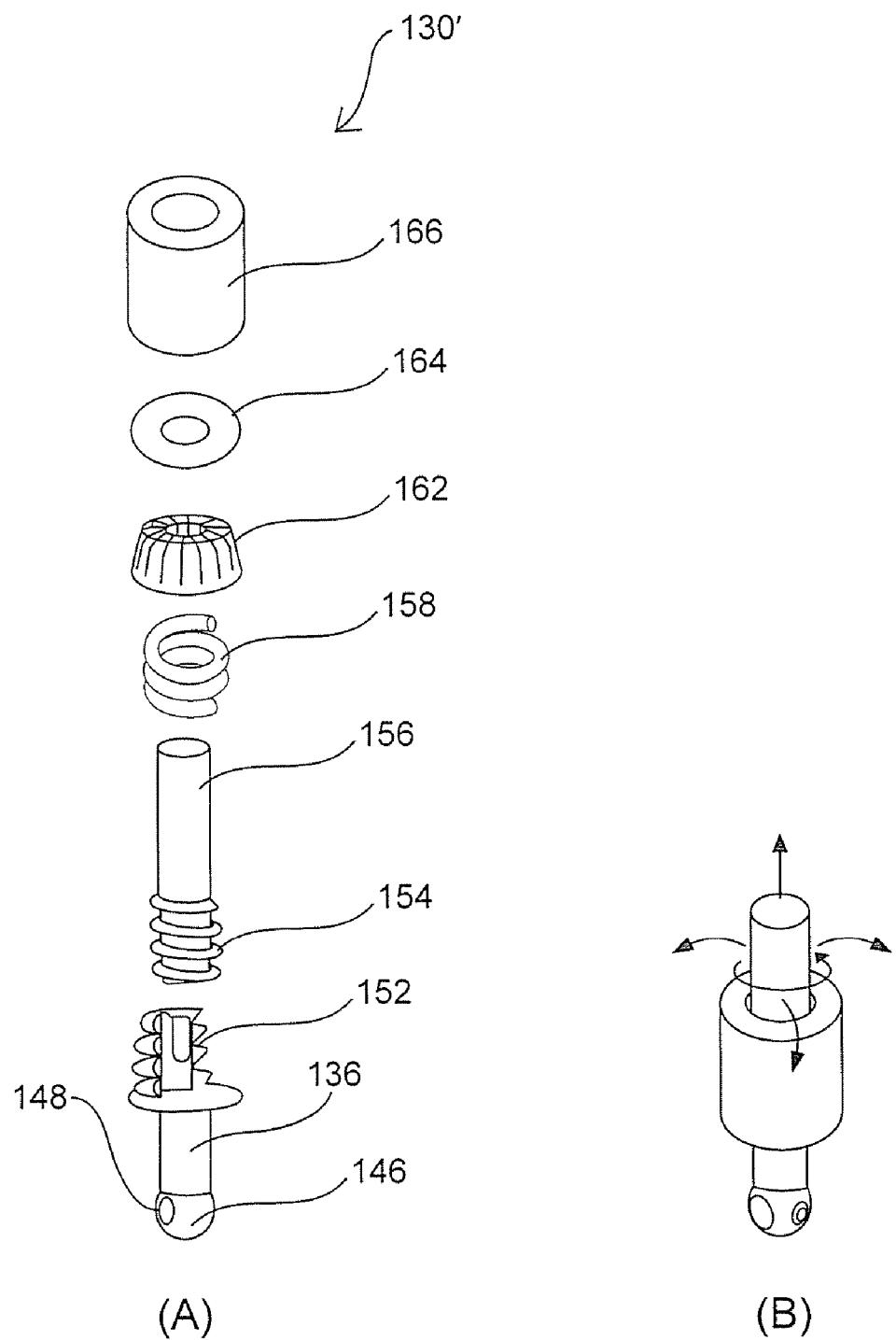
FIGS. 9(A) and 9(B) illustrate a perspective sectional view of a dynamic rod system according to yet another embodiment of the current invention, as well as a depiction of an exemplary range of motion.

Referring to FIG. 9, a further embodiment of a dynamic rod system 130' is shown. Many components are similar to the embodiment of FIG. 6(A). A proximal segment 136 is coupled to a distal segment 156 via a spring 158. A ball end 146 and pins 148 allows coupling of the proximal segment 136 to an assembly such as a hinged assembly coupled to a bone anchor system. The proximal segment has a threaded section 152 and the distal segment has a threaded section 154. A collet 162 may be employed to maintain the dynamic rod 130' in a neutral state. An elastomeric sleeve 164 may then be employed to ensure deleterious material does not clog or otherwise inhibit the action of the collet 162. The elastomeric sleeve may also be employed to keep debris from wear of the device, if any, out of the spinal space. A housing 166 may then be used to seal the dynamic element. FIG. 9(B) shows exemplary ranges of motion provided by this embodiment.

Referring to FIG. 10(A)-(C), a further embodiment of a dynamic rod system 130' is shown. Many components are similar to the embodiment of FIG. 6(A). A proximal segment 168 is coupled to a distal segment 174. The proximal segment 168 has a flange 172 on which is mounted male nub 173. The distal segment 174 is provided with a female receiver 178 affixed to the distal segment at a proximal end 176. A cage spring 184 may be slid over the distal segment 174 and may securely engage the female receiver 178 such that when the female receiver 178 receives the male nub 173, the spring 184 (and in particular a proximal end 186) holds the female receiver 178 and the male nub 173 in a secure fashion.

A separate spring portion 188 may be provided to further enhance the dynamic response. An elastomeric sleeve 192, such as a silicone washer, may then be employed to ensure deleterious material does not clog or otherwise inhibit the action of the spring 184. A housing 194 with top cap 196 may then be used to seal the dynamic element, e.g., by being welded to the flange 172.

FIG. 10(B) shows exemplary ranges of motion provided by this embodiment, and FIG. 10(C) shows a side sectional view of the system of FIG. 10(A).

Figure 10:
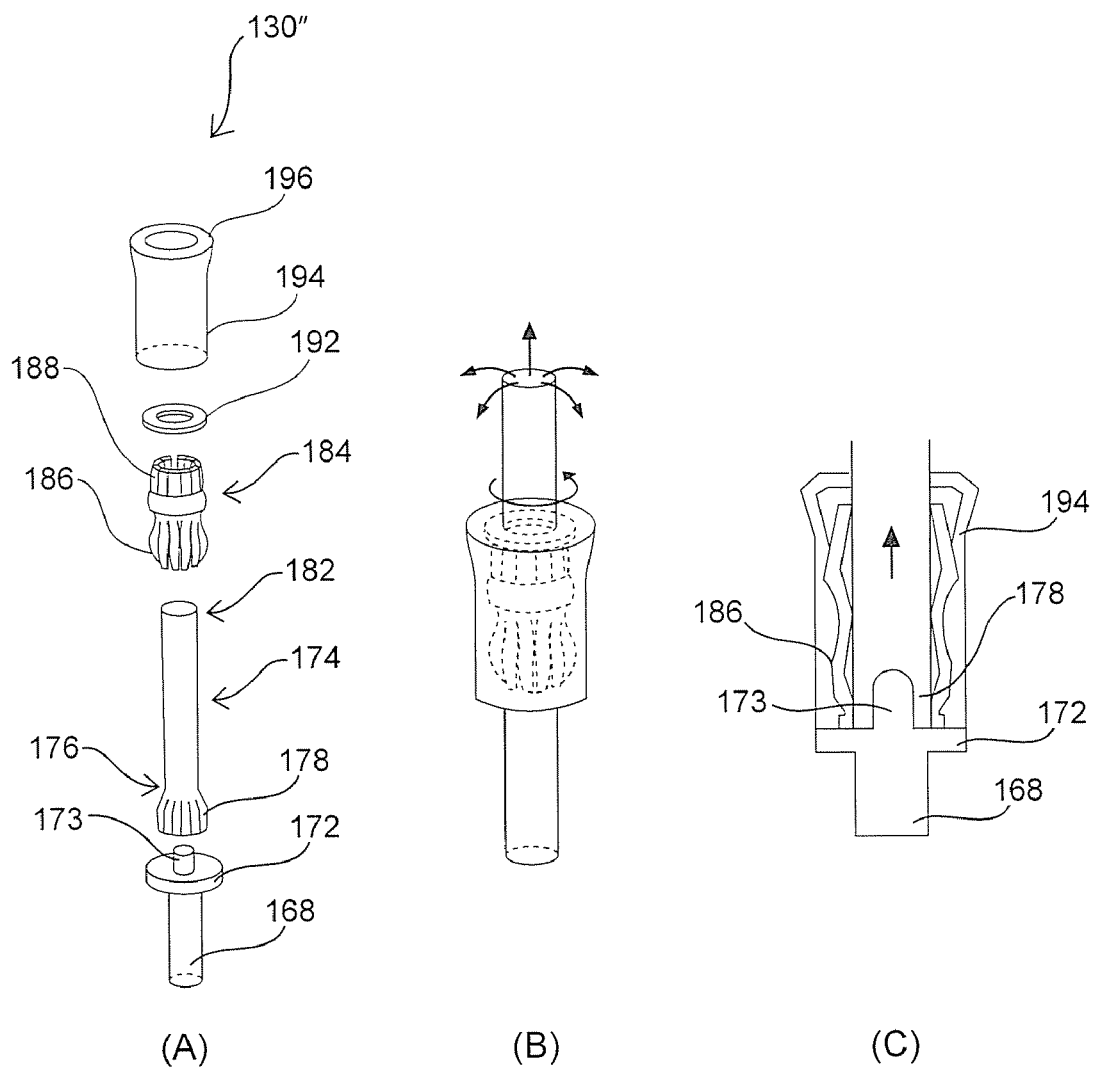
FIG. 10(A)-(C) illustrate perspective and sectional views of a dynamic rod system according to yet another embodiment of the current invention.
Figure 11:
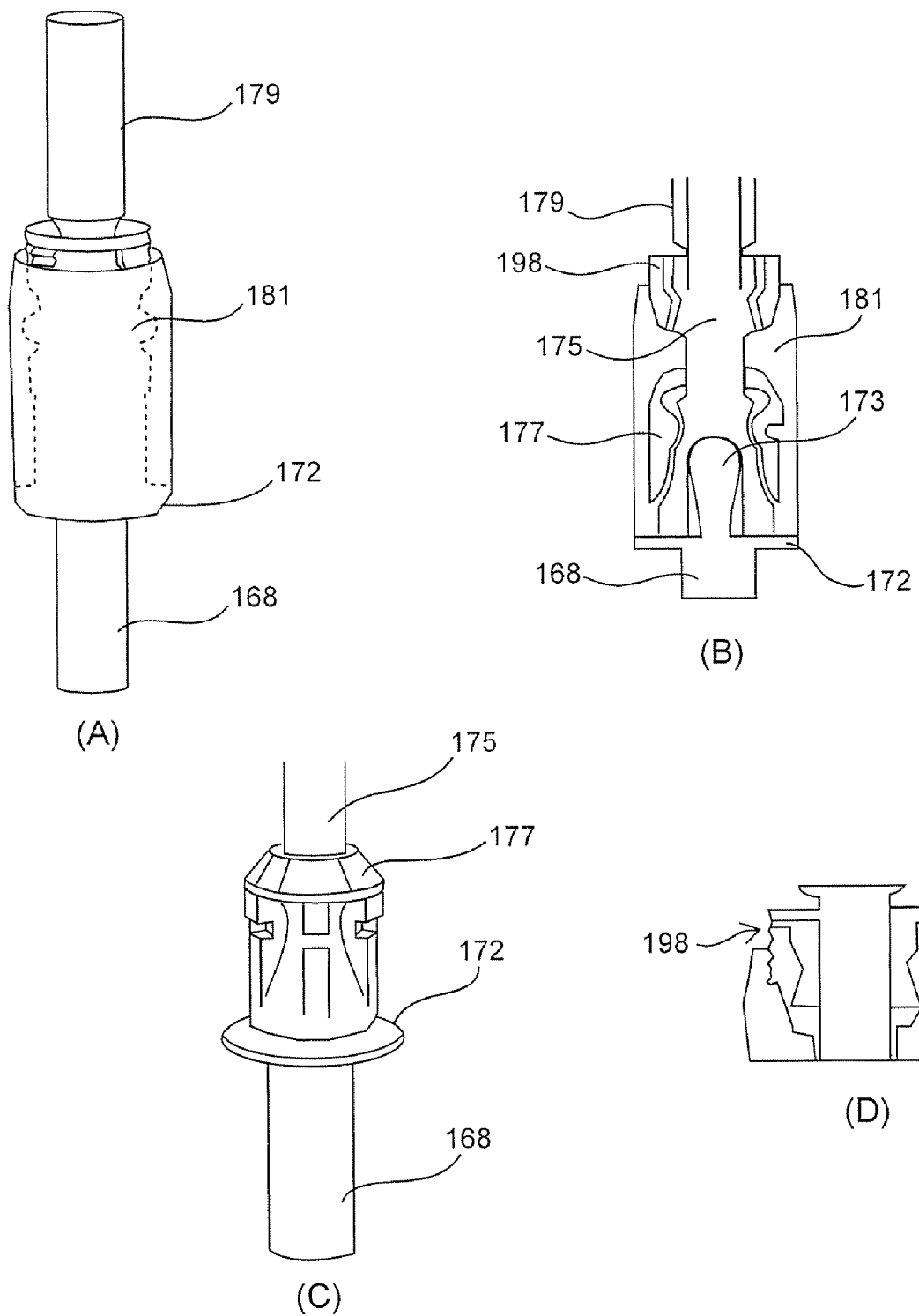
FIG. 11(A)-(D) illustrate perspective and sectional views of a dynamic rod system according to yet another embodiment of the current invention.

FIGS. 11(A)-(D) show an embodiment related to that of FIG. 10. Similar elements perform similar functions, such as the proximal segment 168, flange 172, and male nub 173, and thus no additional description is provided here. However, additional elements include a female rod segment 175 which mates with the male nub 173, a spring 177 which provides extension, torsion, and centering, a rod sleeve 179, and a locking collar 198. An elastomeric sleeve 181 may be employed to performs functions similar to the same component in FIG. 10. As shown in FIG. 11(D), the locking collar may be inserted in various degrees—if fully inserted, a significant amount of motion, or all motion, may be prevented. Lesser insertions result in additional motion allowed.

Referring to FIG. 12(A)-(D), a system 230 is shown in which a proximal segment 202 is coupled to a distal segment 204 by a spring 206 that is attached to each. The spring 206 acts as both to allow torsion and to allow extension. If the spring 206 is sufficiently stiff, it may be the only component that couples the rods. In another embodiment, as shown in the figures and in particular FIG. 12(B), one of the proximal or distal segment may be provided with a ball end 216 which is received by a socket 224 which is coupled to the opposite segment. In FIG. 12(B), the proximal segment is coupled to the ball end and the distal segment carries the socket. In this case, a small gap 222 may be provided in the proximal segment such that the ball end may be partially enclosed by the proximal segment, in particular the distal tip thereof. The amount of bending capable of this dynamic rod system 230 is at least in part determined by the size of the socket. The socket may, in some embodiments, be replaced by fingers (not shown) similar to the way in which a gemstone is held onto a ring setting.

FIG. 12(C) shows exemplary ranges of motion provided by this embodiment.

FIG. 12(D) shows an end view of the system 230. In this embodiment, four fingers 215, 217, 219, and 221 are employed to hold the ball end. As the spring is attached to one or both of the rod segments, a portion of the spring (or another detent if desired, not shown) may contact one of the fingers at minimum and maximum points of torsion, providing a maximum angle φ of torsion.

Figure 13:
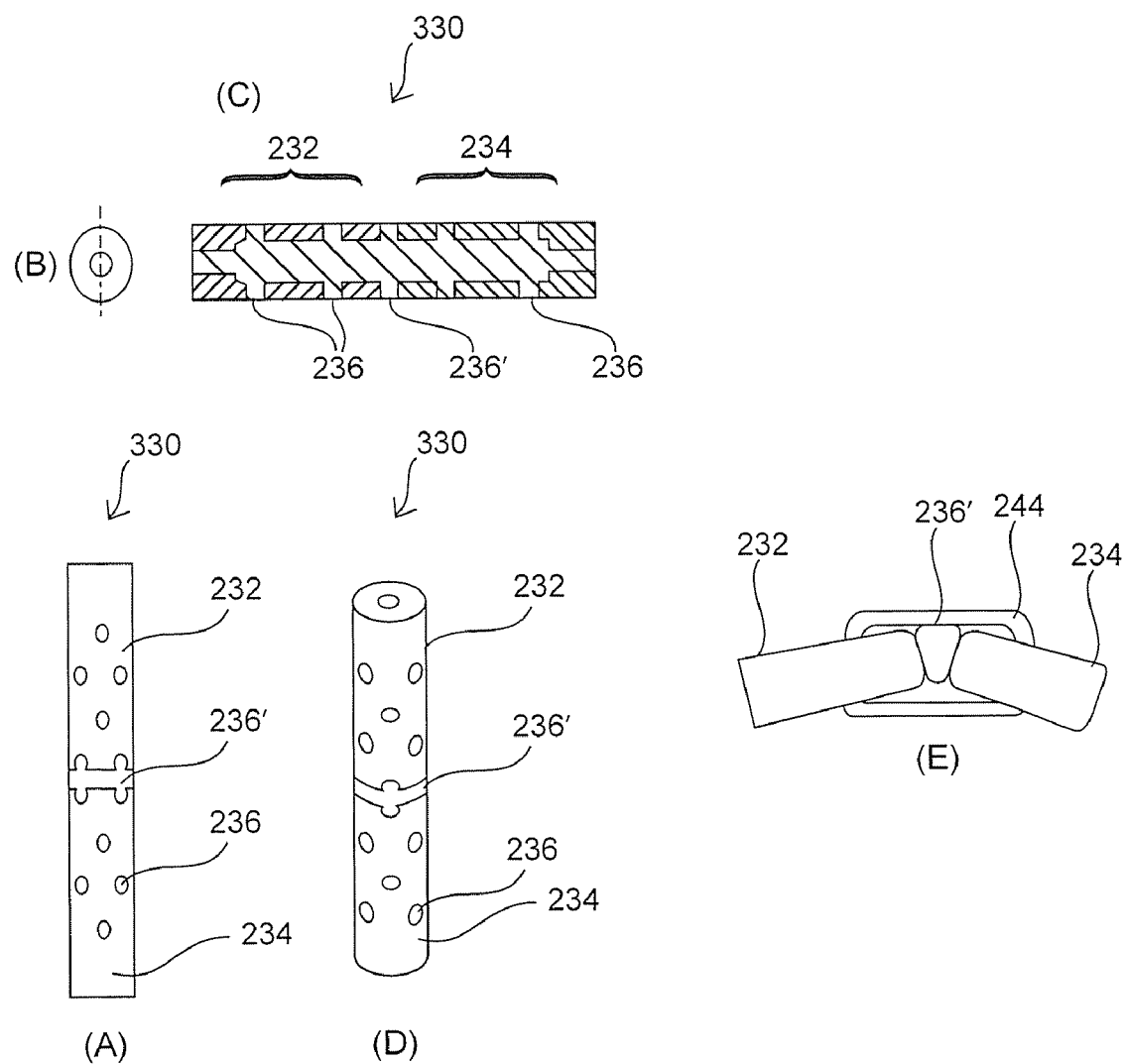
FIG. 13(A)-(E) illustrate side, top, sectional, and perspective views of a dynamic rod system according to yet another embodiment of the current invention.

Referring to FIGS. 13(A)-(E), an embodiment of a dynamic rod system 330 is shown. In this embodiment, a proximal segment 232 is coupled to a distal segment 234. The proximal and distal segments are each made of a rigid material, e.g., titanium, but a plurality of holes 236 are provided that are filled with a flexible material such as an elastomeric material. The elastomeric material also forms a hinge portion 236'. FIG. 13(B) shows an end sectional view of the system, and FIG. 13(C) shows a side view. Referring to FIG. 13(E), the system is shown with an optional outer sleeve 244 which may be employed to limit the amount of angular flexion afforded by the system.

Figure 14:
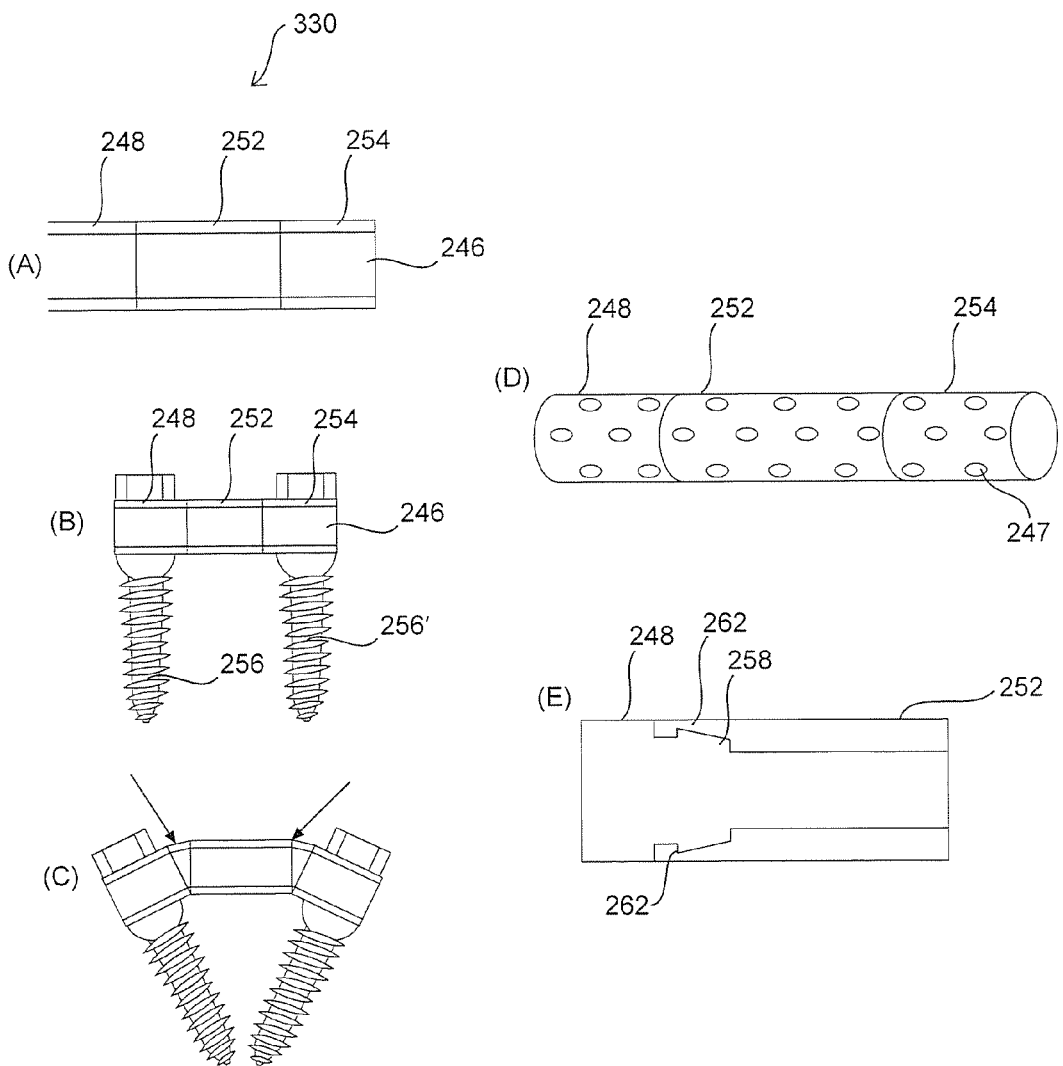
FIG. 14(A)-(E) illustrate various views of a dynamic rod system according to yet another embodiment of the current invention.

Referring to FIGS. 14(A)-(E), another embodiment of a dynamic rod system 430 is shown with three component sleeves 248, 252, and 254. Disposed throughout the center of the sleeves is an elastomeric material 246. When the dynamic rod system 430 is coupled in known fashion to pedicle screws 256 and 256', as shown in FIGS. 14(B) and 14(C), the pedicle screws are allowed to hingedly rotate to provide a dynamic spinal support system. An additional benefit is that pedicle screws 256 and 256' may be dynamically joined even where the installation of the pedicle screws 256 and 256' has resulted in their screw heads being misaligned. As shown in FIG. 14(D), a plurality of holes 247 may be provided to enhance flexibility. Finally, as shown in FIG. 14(E), a feature may be provided to limit the amount of bending allowed by the system. A sleeve extension 258 may be mated with a frusto-conical member 262 at the intersection of two adjoining sleeves, e.g., sleeves 248 and 252. In this way, sleeves 248 and 252 may be bent at an angle at most equal to the angle of the frusto-conical section. A motion-limiting collar such as described above may also be employed for similar purposes.

Figure 15:
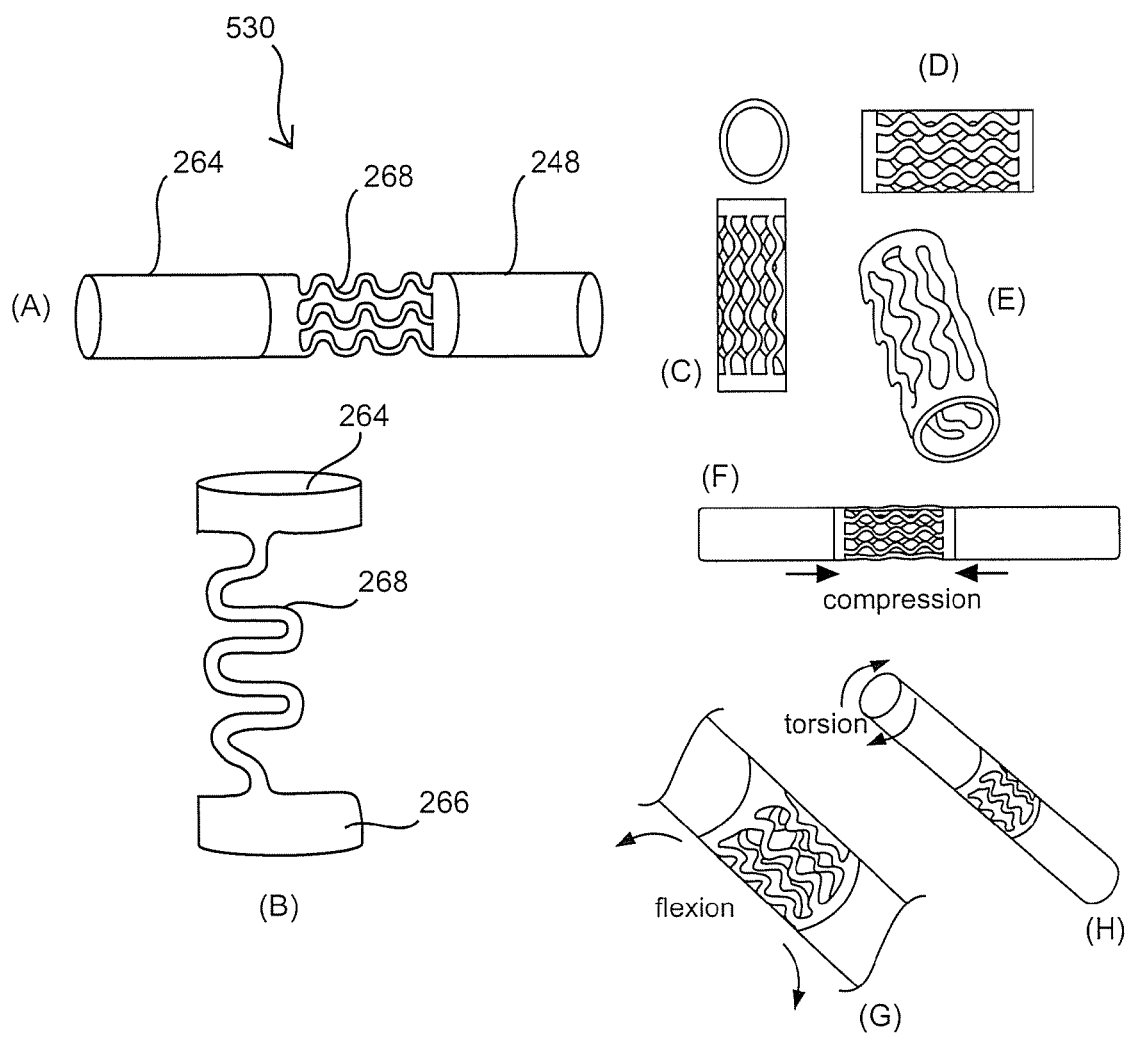
FIG. 15(A)-(H) illustrate various views of a dynamic rod system according to yet another embodiment of the current invention.

FIGS. 15(A)-(H) show views of another embodiment of a dynamic rod system 530, a proximal segment 264 is joined to a distal segment 266 by a dynamic element 268. The dynamic element is formed by a series of semi-rigid serpentine filaments which distribute support for the spinal components, to which the segments are affixed, in a known fashion. The serpentine filaments may be formed of various materials, including titanium and associated alloys, stainless steel and associated alloys, polymers such as PEEK and other biocompatible materials. FIGS. 15(C)-(E) show views of the serpentine filaments from various angles, while FIGS. 15(F)-(H) show exemplary ranges of motion provided by this embodiment.

The serpentine filaments may differ amongst themselves in mechanical properties, resulting in preferred directions of motion. The same may result from different densities of filaments. Besides the filaments, the volume between the proximal and distal segments may include a flexible material such as an elastomer.

FIGS. 16(A)-(C) show views of embodiments of the dynamic rods in use, i.e., dynamic rods 300 and 310 span pedicle screw systems 304/308 and 302/306.

As noted above, various MIS systems, such as those incorporated by reference above, may include dynamic rods according to the present invention. In some cases, a dynamic rod system may be installed on each side of a vertebral segment. Depending on the treatment, the rod systems may be alike or may differ in mechanical properties, such as maximum amounts of extension or compression, angular flexion, and rotation or torsion. They may also be alike or differ in their respective restoring forces.

Referring to FIG. 17(A)-(B), the dynamic rod embodiments may be employed in a multi-level system, such as may span three vertebral segments 312, 314, and 316, with three screw systems on each side of the spinous processes. In FIG. 17(A), the non-primed components are disposed on the right side of the spinous process and primed components are disposed on the left side. A long rod may be employed that spans all three segments, and that has a segment 326 with no dynamic element between first and second screws 328 and 322 but which incorporates a dynamic element 332 on a segment 328 between the second and third screws 322 and 324. The description for the primed components is analogous. In such systems, movement is allowed but support is enhanced to the fused segments, and thus stress is distributed to reduce the increased amount at the level above the fusion site. Given this teaching it is clear other possibilities may be envisioned as well. Moreover, in some multi-level procedures, the same intermediate pedicle screw may be employed to secure both the upper and lower rods, whether rigid or dynamic.

In another variation of the above embodiments, a chosen vertebral segment and thus set of pedicles is skipped, but a dynamic rod spans the vertebral segments above and below the chosen vertebral segments. This embodiment may be called for when the chosen vertebral segment is too damaged to install pedicle screws, e.g., was damaged by a gunshot or other acute localized injury. In this embodiment, pedicle screws are installed in the vertebral segments above and below the chosen vertebral segment, and a dynamic rod is installed that is typically longer than the dynamic rods disclosed above. Either the rod may be made longer or the dynamic component may be made longer or both. In this type of embodiment, the dynamic nature is especially important as the motion of three vertebral segments is being tied together, and much freedom of motion may be sacrificed without a dynamic element.

In methods according to embodiments of the invention, the above-described dynamic rod is substituted for the rigid rods described in the applications incorporated by reference above. The same pedicle screws may still be employed. In other words, a rigid rod is removed and a dynamic rod according to the invention is inserted in its place. In an alternative embodiment of the method, a dynamic rod is removed and a rigid rod in inserted in its place. In any case, the dynamic rods of the above description may be inserted in pre-existing pedicle screws, no matter the placement or the type.

The procedures above may be performed in combination with other procedures, including facet procedures such as facet replacement or augmentation.

In other methods according to embodiments of the invention, various properties of the dynamic rod are adjusted before, during, or after implantation. These properties include: adjusting the limit of travel, such as via set screws; adjusting the amount of restoring force, again such as via set screws or other means; adjusting travel such as via a tapered collet that slides over the rod and that employs a thread that when tightened securely engages the taper. In a corresponding method, the dynamic rod may be placed adjacent to a vertebral segment that has a fixed or rigid rod in place. In this way, the dynamic rod acts as a prophylactic to prevent degradation of adjacent segments. In such a procedure, the dynamic rod may be placed on one or both sides, to distribute stress more evenly in a reduced or ramped fashion.

The components of the devices of the present invention are preferably configured for percutaneous placement, each device sized for placement through a percutaneous cannula. Each device preferably includes a lumen or sidecar through which a guidewire can be placed, or allowing placement alongside a percutaneously placed guidewire. The dynamic rod of the present invention can preferably be rotated or pivoted out of the cannula toward the receiving pedicle screw assembly, such as with the inclusion of a slot allowing the guidewire to exit a lumen, while a guidewire is in place. The dynamic rod and attached components are preferably configured such that the dynamic rod can be secured, such as with insertion of multiple set screws, also with a guidewire in place. Other components may include slot exits from guidewire lumens such as to allow over-the-wire delivery and subsequent escape of the guidewire while leaving the guidewire in place. The devices and methods of the present invention are configured to be inserted without resection of tissue, however procedures including or requiring resection are also supported.

It should be noted that the description above refers to specific examples of the invention, but that the scope of the invention is to be limited only by the scope of the claims appended hereto. Moreover, the sizes and materials shown for the components of the system may vary, but certain ranges of sizes and materials have been shown to be of particular use.

For example, the bone anchors, i.e., pedicle screws, shown may have exemplary lengths ranging from 25 to 80 mm, and may, e.g., be available within that range in 5 mm increments. The diameters of the same may be, e.g., 5.5 mm, 6.0 mm, 6.5 mm, etc. They may be made of metal, such as a titanium alloy, e.g., Ti-6A1-4V, ELI, etc. They may also be made of stainless steel, e.g., 316LSS or 22-13-5SS. The holes into which the same are inserted may be pre-tapped, or alternatively the pedicle screws may be self-tapping. If the bone anchor has a receiving slot, such as a hex head or other such head, then a screwdriver may be used to attach to the bone anchor directly. Once the pivoting rod is in place, a screwdriver may attach to the pivoting rod for further rotation. The pivoting rod itself may be used to further drive the screw. The bone anchors may further have either fixed or polyaxial heads. Their threads may be standard, may be cutting threads, may incorporate flutes at their distal end, or may be any other type of thread. The bone anchors need not be purely of a screw-type. Rather they may also be soft-tissue-type anchors, such as a cylindrical body with a Nitinol barb.

The dynamic rods shown may have exemplary lengths ranging from 30 to 85 mm, and may, e.g., be available within that range in 5 mm increments. The diameters of the same may be, e.g., 5.5 mm, etc. They may be made of metal, such as CP Titanium Grade 2, stainless steel, etc.

The ranges of motion accommodated by the system may be as follows: the extension allowed may be zero up to 1 mm, the angular flexion may be zero up to 5 degrees, the torsional deflection zero may be up to 15 degrees. The system may provide for a restoring force back to a neutral or equilibrium position or state.

While not shown in the figures, the distal end of the distal segment may be fitted with a feature to assist in the engagement of the distal segment with the second bone anchor or other such receiving assembly. Moreover, the ends of the dynamic rod need not connect directly into bone screw assemblies. The same may connect to couplers or to other components as well.

The dynamic rod may be contoured prior to insertion. In other words, to more closely match the curvature of a spine, or for increased strength, i.e., to accommodate the geometry of the pedicle bone screws, or to accommodate the geometry of the spinal segment in which it is installed, a curve or other contour may be designed into the rod prior to insertion. Alternatively, a physician may bend the rod or put another such contour into the rod, either manually or with the aid of a device, prior to insertion. In certain cases, the rod may be contoured after insertion or partial insertion, such as after a measurement procedure is performed to determine the optimal contour angles for that particular patient.

Further, systems according to the disclosed embodiments may be disposed not only on multiple levels of the vertebrae but also on different sides of the spinous process. In other words, two systems may be disposed in a single segment, one on each pedicle. Moreover, the use of the disclosed pedicle-screw-based systems may be employed in combination with various spacer systems, such as are disclosed in U.S. Non-Provisional patent application Ser. No. 11/314,712, filed Dec. 20, 2005, assigned to the assignee of the present invention and herein incorporated by reference in its entirety.

The sleeve caps or housings, as well as other components, may incorporate radiolucent or radiotransparent materials so that the installing surgeon or other physician may view the dynamic elements within under fluoroscopy or other such techniques. Changes in material density, such as "notches", may be employed to indicate the state of various components, e.g., via use of X-rays. The sleeve caps or housings may be made flexible to provide a small amount of dynamic motions per se. Additionally or alternatively, other types of markers may be used to enable viewing of the dynamic elements such as visible markers, ultrasonic markers, magnetic markers or other markers.

The devices may be provided in kit form, where the kits may include multiple springs from which the surgeon can choose to select desired properties. In the same way, kits may provide multiple housings among which a housing may be chosen for similar reasons.

Markers may be employed to indicate the status of the dynamic rod. For example, the markers may indicate the amount of extension or compression, rotation, or angular flexion. Such markers may also indicate the amount of stress the dynamic rod is subjected to. Such markers may be visible, radioopaque, ultrasonic, magnetic, or a combination of these. The markers may also be integrated onto the dynamic coupler, sleeve cap, or housing.

While the figures have generally shown the dynamic elements substantially in the center of the dynamic rods, the same may be disposed at any position on the rod, including the ends.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A bone stabilization device for a patient in which first and second bone anchors are attached to bone at first and second locations respectively, the bone anchors coupled by at least one dynamic rod, wherein the dynamic rod comprises:
    a proximal segment and a distal segment, the proximal segment coupled to a first bone anchor and the distal segment coupled to a second bone anchor;
    wherein the proximal segment is joined to the distal segment at a dynamic element that includes:
        a distal threaded section having helical grooves, the distal threaded section disposed at a distal end of the proximal segment;
        a proximal threaded section having helical grooves, the proximal threaded section disposed at a proximal end of the distal segment;
        a spring configured to joinedly couple the distal threaded section and the proximal threaded section;
        a housing substantially surrounding the dynamic element; and
        an elastomeric material positioned in the housing;
    wherein coils of the spring are configured to be received in and correspond to the helical grooves of the distal threaded section and the helical grooves of the proximal threaded section.

2. The device of claim 1, wherein the proximal and distal threaded section comprise partial screw threads.

3. The device of claim 1, wherein the proximal and distal sections are collinear when in an equilibrium condition.

4. The device of claim 1, further comprising engagement means on a proximal end of the proximal segment and on a distal end of the distal segment, for coupling to a pedicle screw.

5. The device of claim 4, wherein the engagement means is selected from the group consisting of: a hinge; a hole; and a threaded hole.

6. The device of claim 1, wherein the spring has a circular cross section.

7. The device of claim 1, wherein the spring has an oval cross section.

8. A minimally invasive bone stabilization system comprising:
    a proximal segment and a distal segment, the proximal segment coupled to a first bone anchor and the distal segment coupled to a second bone anchor;
    wherein the proximal segment is joined to the distal segment at a dynamic element that includes:
        a distal section having helical grooves, the distal section disposed at a distal end of the proximal segment;
        a proximal section having helical grooves, the proximal section disposed at a proximal end of the distal segment;
        a spring configured to encompass the distal section and the proximal section wherein coils of the spring are received in the helical grooves of the distal section and the proximal section; and
    a slotted dilator device comprising:
        at least one tube with a proximal end and a distal end, and a longitudinal slot extending proximally from said distal end;
        wherein said longitudinal slot is configured such that the dynamic element rotates through the slot to a location outside said tube.

9. The system of claim 8, further comprising a housing substantially surrounding the dynamic element.

10. The system of claim 9, further comprising an elastomeric material positioned in the housing.

11. The system of claim 8, wherein the dynamic rod is structured and configured to allow extension of up to approximately 1.0 mm, angular flexion of up to approximately 5 degrees, and torsional rotation of up to approximately 15 degrees.

12. The system of claim 8, wherein the proximal and distal sections are collinear when in an equilibrium condition.

13. The system of claim 8, further comprising engagement means on a proximal end of the proximal segment and on a distal end of the distal segment, for coupling to a pedicle screw.

14. The system of claim 13, wherein the engagement means is selected from the group consisting of: a hinge; a hole; and a threaded hole.

15. The system of claim 8, wherein the spring has a circular cross section.

16. The system of claim 8, wherein the spring has an oval cross section.

17. A bone stabilization device for a patient in which first and second bone anchors are attached to bone at first and second locations respectively, the bone anchors coupled by at least one dynamic rod, wherein the dynamic rod comprises:
   a proximal segment and a distal segment, the proximal segment coupled to a first bone anchor and the distal segment coupled to a second bone anchor;
   wherein the proximal segment is joined to the distal segment at a dynamic element that includes:
   a distal threaded section having helical grooves, the distal threaded section disposed at a distal end of the proximal segment;
   a proximal threaded section having helical grooves, the proximal threaded section disposed at a proximal end of the distal segment; and
   a spring configured to joinedly couple the distal threaded section and the proximal threaded section;
   wherein coils of the spring are configured to be received in and correspond to the helical grooves of the distal threaded section and the helical grooves of the proximal threaded section; and
   wherein the dynamic rod is structured and configured to allow extension of up to approximately 1.0 mm, angular flexion of up to approximately 5 degrees, and torsional rotation of up to approximately 15 degrees.

18. The device of claim 17, wherein the proximal and distal threaded section comprise partial screw threads.

19. The device of claim 17, wherein the proximal and distal sections are collinear when in an equilibrium condition.

20. The device of claim 17, further comprising engagement means on a proximal end of the proximal segment and on a distal end of the distal segment, for coupling to a pedicle screw.

21. The device of claim 20, wherein the engagement means is selected from the group consisting of: a hinge; a hole; and a threaded hole.

22. The device of claim 17, wherein the spring has a circular cross section.

23. The device of claim 17, wherein the spring has an oval cross section.

* * * * *

UNITED STATES PATENT AND TRADEMARK OFFICE
CERTIFICATE OF CORRECTION

PATENT NO. : 7,935,134 B2  
APPLICATION NO. : 11/427738  
DATED : May 3, 2011  
INVENTOR(S) : Reglos et al.

Page 1 of 1

It is certified that error appears in the above-identified patent and that said Letters Patent is hereby corrected as shown below:

On title page

Please revise the section presented below to read as follows:

Related U.S. Application Data:

Item (63) Continuation-in-part of application No. 11/436,407, filed on May 17, 2006, which is a continuation-in-part of application No. 11/033,452 filed on Jan. 10, 2005, which is a continuation-in-part of application No. 11/006,495, filed Dec. 6, 2004, and a continuation-in-part of application No. 10/970,366, filed Oct. 20, 2004, and said application No. 11/436,407, filed May 17, 2006, is a continuation-in-part of application No. 11/362,366, filed February 23, 2006, which claims benefit of Provisional application No. 60/701,660 filed July 22, 2005.

Signed and Sealed this  
Thirteenth Day of September, 2011

David J. Kappos  
*Director of the United States Patent and Trademark Office*